(12) United States Patent
Miller et al.

(10) Patent No.: US 8,998,848 B2
(45) Date of Patent: Apr. 7, 2015

(54) INTRAOSSEOUS DEVICE AND METHODS FOR ACCESSING BONE MARROW IN THE STERNUM AND OTHER TARGET AREAS

(75) Inventors: Larry J. Miller, Spring Branch, TX (US); Robert W. Titkemeyer, San Antonio, TX (US); David S. Bolleter, San Antonio, TX (US); Ruben Trevino, San Antonio, TX (US); Matthew T. Harmon, Santa Cruz, CA (US); Christopher Kilcoin, Santa Cruz, CA (US)

(73) Assignee: Vidacare LLC, Shavano Park, TX (US)

( * ) Notice: Subject to any disclaimer, the term of this patent is extended or adjusted under 35 U.S.C. 154(b) by 2273 days.

(21) Appl. No.: 11/620,927

(22) Filed: Jan. 8, 2007

(65) Prior Publication Data
US 2007/0270775 A1 Nov. 22, 2007

Related U.S. Application Data

(63) Continuation-in-part of application No. 10/987,051, filed on Nov. 12, 2004.

(51) Int. Cl.
| | |
|---|---|
| *A61M 5/00* | (2006.01) |
| *A61N 1/30* | (2006.01) |
| *A61M 31/00* | (2006.01) |
| *A61M 5/46* | (2006.01) |
| *A61B 10/02* | (2006.01) |

(52) U.S. Cl.
CPC ............... *A61B 10/025* (2013.01); *A61M 5/46* (2013.01); *A61B 2010/0258* (2013.01)

(58) Field of Classification Search
CPC .. A61B 10/025; A61B 10/0233; A61B 10/00; A61B 10/0258; A61M 5/46; A61M 5/00; A61M 3/00
USPC ............. 604/19, 48, 117, 506, 507, 187, 116, 604/181, 21; 606/80
See application file for complete search history.

(56) References Cited

U.S. PATENT DOCUMENTS

| | | | |
|---|---|---|---|
| 1,539,637 A | 5/1925 | Bronner | |
| 2,317,648 A | 4/1943 | Siqveland | ............ 32/26 |

(Continued)

FOREIGN PATENT DOCUMENTS

| | | | |
|---|---|---|---|
| CA | 2138842 | 6/1996 | ............ A61M 19/00 |
| CA | 2 454 600 | 1/2004 | ............ A61B 10/00 |

(Continued)

OTHER PUBLICATIONS

Non-Final Office Action, U.S. Appl. No. 10/449,476, 8 pages, Oct. 29, 2008.

(Continued)

*Primary Examiner* — Kevin C Sirmons
*Assistant Examiner* — Bradley G Thomas, Jr.
(74) *Attorney, Agent, or Firm* — Norton Rose Fulbright US LLP

(57) ABSTRACT

Apparatus and methods are provided to access bone marrow at various target areas. Such apparatus may include an intraosseous device operable to penetrate bone at a selected target area and a depth limiter operable to control depth of penetration of the intraosseous device into bone and associated bone marrow. A manual driver and a guide may be included to optimize optimum insertion of the intraosseous device at a selected insertion site on a sternum.

30 Claims, 7 Drawing Sheets

(56) References Cited

U.S. PATENT DOCUMENTS

| | | | |
|---|---|---|---|
| 2,419,045 A | 4/1947 | Whittaker | 128/305 |
| 2,773,501 A | 12/1956 | Young | 128/221 |
| 2,860,635 A | 11/1958 | Wilburn et al. | 604/190 |
| 3,104,448 A | 9/1963 | Morrow et al. | |
| 3,120,845 A | 2/1964 | Horner | 128/310 |
| 3,173,417 A | 3/1965 | Horner | 128/305 |
| 3,175,554 A | 3/1965 | Stewart | 128/2 |
| 3,507,276 A | 4/1970 | Burgess et al. | 128/173 |
| 3,543,966 A | 12/1970 | Ryan et al. | 222/94 |
| 3,750,667 A | 8/1973 | Pshenichny et al. | 604/117 |
| 3,815,605 A | 6/1974 | Schmidt et al. | 128/305 |
| 3,835,860 A | 9/1974 | Garreston et al. | 128/310 |
| 3,893,445 A | 7/1975 | Hofsess | 128/2 B |
| 3,991,765 A | 11/1976 | Cohen | 128/305 |
| 4,021,920 A | 5/1977 | Kirschner et al. | 32/28 |
| 4,046,254 A | 9/1977 | Kramer | 206/370 |
| 4,099,518 A | 7/1978 | Baylis et al. | 600/567 |
| 4,124,026 A | 11/1978 | Berner et al. | 128/303 R |
| 4,142,517 A * | 3/1979 | Contreras Guerrero de Stavropoulos et al. | 600/567 |
| 4,170,993 A | 10/1979 | Alvarez | 128/214 R |
| 4,185,619 A | 1/1980 | Reiss | 128/1.1 |
| 4,194,505 A | 3/1980 | Schmitz | 128/218 |
| 4,258,722 A | 3/1981 | Sessions et al. | 128/753 |
| 4,262,676 A | 4/1981 | Jamshidi | 128/753 |
| 4,266,555 A | 5/1981 | Jamshidi | 600/566 |
| 4,306,570 A | 12/1981 | Matthews | 128/754 |
| 4,333,459 A | 6/1982 | Becker | 128/218 |
| 4,381,777 A | 5/1983 | Garnier | 604/188 |
| 4,399,723 A | 8/1983 | Marleau | 81/437 |
| 4,441,563 A | 4/1984 | Walton, II | 173/163 |
| 4,469,109 A | 9/1984 | Mehl | 128/753 |
| 4,484,577 A | 11/1984 | Sackner et al. | 128/203.28 |
| 4,487,209 A | 12/1984 | Mehl | 600/567 |
| 4,543,966 A | 10/1985 | Islam et al. | 128/754 |
| 4,553,539 A | 11/1985 | Morris | 128/132 D |
| 4,605,011 A | 8/1986 | Naslund | 128/752 |
| 4,620,539 A | 11/1986 | Andrews et al. | 128/303 |
| 4,646,731 A | 3/1987 | Brower | 128/156 |
| 4,654,492 A | 3/1987 | Koerner et al. | 200/153 P |
| 4,655,226 A | 4/1987 | Lee | 128/754 |
| 4,659,329 A | 4/1987 | Annis | 604/180 |
| 4,692,073 A | 9/1987 | Martindell | 408/239 A |
| 4,711,636 A | 12/1987 | Bierman | 604/180 |
| 4,713,061 A | 12/1987 | Tarello et al. | 604/200 |
| 4,716,901 A | 1/1988 | Jackson et al. | 128/343 |
| 4,723,945 A | 2/1988 | Theiling | 604/232 |
| 4,762,118 A | 8/1988 | Lia et al. | 128/4 |
| 4,772,261 A | 9/1988 | Von Hoff et al. | 604/51 |
| 4,787,893 A | 11/1988 | Villette | 604/188 |
| 4,793,363 A | 12/1988 | Ausherman et al. | 128/754 |
| 4,838,282 A | 6/1989 | Strasser et al. | 600/567 |
| 4,844,259 A | 7/1989 | Glowczewskie, Jr. et al. | 206/370 |
| 4,867,158 A | 9/1989 | Sugg | 128/305 |
| 4,919,146 A | 4/1990 | Rhinehart et al. | 128/752 |
| 4,921,013 A | 5/1990 | Spalink et al. | 137/614.05 |
| 4,922,602 A | 5/1990 | Mehl | 29/460 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A | 11/1990 | Kramer et al. | 604/51 |
| 4,986,279 A | 1/1991 | O'Neill | 128/754 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller et al. | 604/49 |
| 5,133,359 A | 7/1992 | Kedem | 128/754 |
| 5,137,518 A | 8/1992 | Mersch | 604/168 |
| 5,139,500 A | 8/1992 | Schwartz | 606/96 |
| RE34,056 E | 9/1992 | Lindgren et al. | 128/754 |
| 5,172,701 A | 12/1992 | Leigh | 128/753 |
| 5,172,702 A | 12/1992 | Leigh et al. | 128/754 |
| 5,176,415 A | 1/1993 | Choksi | 285/331 |
| 5,176,643 A | 1/1993 | Kramer et al. | 604/135 |
| 5,195,985 A | 3/1993 | Hall | 604/195 |
| 5,203,056 A | 4/1993 | Funk et al. | 24/543 |
| 5,207,697 A | 5/1993 | Carusillo et al. | 606/167 |
| 5,249,583 A | 10/1993 | Mallaby | 128/754 |
| 5,257,632 A | 11/1993 | Turkel et al. | 128/754 |
| 5,269,785 A | 12/1993 | Bonutti | 606/80 |
| 5,279,306 A | 1/1994 | Mehl | 128/753 |
| 5,312,351 A | 5/1994 | Gerrone | 604/117 |
| 5,312,364 A | 5/1994 | Jacobs | 604/180 |
| 5,312,408 A | 5/1994 | Brown | 606/80 |
| 5,324,300 A | 6/1994 | Elias et al. | 606/180 |
| 5,332,398 A | 7/1994 | Miller et al. | 604/175 |
| 5,333,790 A | 8/1994 | Christopher | 239/391 |
| 5,341,816 A | 8/1994 | Allen | 600/567 |
| 5,341,823 A | 8/1994 | Manosalva et al. | 128/898 |
| 5,348,022 A | 9/1994 | Leigh et al. | 128/753 |
| 5,356,006 A | 10/1994 | Alpern et al. | 206/363 |
| 5,357,974 A | 10/1994 | Baldridge | 128/754 |
| 5,368,046 A * | 11/1994 | Scarfone et al. | 600/567 |
| 5,372,583 A | 12/1994 | Roberts et al. | 604/51 |
| 5,383,859 A | 1/1995 | Sewell, Jr. | 604/164 |
| 5,385,151 A | 1/1995 | Scarfone et al. | 600/567 |
| 5,385,553 A | 1/1995 | Hart et al. | 604/167 |
| 5,400,798 A | 3/1995 | Baran | 128/754 |
| 5,405,348 A | 4/1995 | Anspach et al. | 606/80 |
| 5,405,362 A | 4/1995 | Kramer et al. | 607/5 |
| 5,423,824 A | 6/1995 | Akerfeldt et al. | 606/80 |
| 5,431,655 A | 7/1995 | Melker et al. | 606/79 |
| 5,451,210 A | 9/1995 | Kramer et al. | 604/137 |
| 5,484,442 A | 1/1996 | Melker et al. | 606/79 |
| D369,858 S | 5/1996 | Baker et al. | D24/112 |
| 5,514,097 A | 5/1996 | Knauer | 604/136 |
| 5,526,821 A | 6/1996 | Jamshidi | 128/753 |
| 5,529,580 A | 6/1996 | Kusunoki et al. | 606/170 |
| 5,549,565 A | 8/1996 | Ryan et al. | 604/167 |
| 5,554,154 A | 9/1996 | Rosenberg | 606/80 |
| 5,556,399 A | 9/1996 | Huebner | 606/80 |
| 5,558,737 A | 9/1996 | Brown et al. | 156/172 |
| 5,571,133 A | 11/1996 | Yoon | 606/185 |
| 5,586,847 A | 12/1996 | Mattern, Jr. et al. | 408/239 A |
| 5,591,188 A | 1/1997 | Waisman | 606/182 |
| 5,595,186 A | 1/1997 | Rubinstein et al. | 128/754 |
| 5,601,559 A | 2/1997 | Melker et al. | 606/79 |
| 5,632,747 A | 5/1997 | Scarborough et al. | |
| 5,672,155 A | 9/1997 | Riley et al. | 604/154 |
| 5,713,368 A | 2/1998 | Leigh | 128/753 |
| 5,724,873 A | 3/1998 | Hillinger | 81/451 |
| 5,733,262 A | 3/1998 | Paul | 604/116 |
| 5,752,923 A | 5/1998 | Terwilliger | 600/562 |
| 5,762,639 A | 6/1998 | Gibbs | 604/272 |
| 5,766,221 A | 6/1998 | Benderev et al. | 606/232 |
| 5,769,086 A | 6/1998 | Ritchart et al. | 128/753 |
| 5,779,708 A | 7/1998 | Wu | 606/80 |
| 5,800,389 A | 9/1998 | Burney et al. | 604/93 |
| 5,807,275 A | 9/1998 | Jamshidi | 600/567 |
| 5,807,277 A | 9/1998 | Swaim | 600/567 |
| 5,810,826 A | 9/1998 | Akerfeldt et al. | 606/80 |
| 5,817,052 A | 10/1998 | Johnson et al. | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |
| 5,868,711 A | 2/1999 | Kramer et al. | 604/136 |
| 5,868,750 A | 2/1999 | Schultz | 606/104 |
| 5,873,499 A | 2/1999 | Leschinsky et al. | 222/327 |
| 5,873,510 A | 2/1999 | Hirai et al. | 227/130 |
| 5,885,226 A | 3/1999 | Rubinstein et al. | 600/564 |
| 5,891,085 A | 4/1999 | Lilley et al. | 604/68 |
| 5,911,701 A | 6/1999 | Miller et al. | 604/22 |
| 5,911,708 A | 6/1999 | Teirstein | 604/183 |
| 5,916,229 A | 6/1999 | Evans | 606/171 |
| 5,919,172 A | 7/1999 | Golba, Jr. | 604/272 |
| 5,921,987 A | 7/1999 | Stone | 606/80 |
| 5,924,864 A | 7/1999 | Loge et al. | 433/118 |
| 5,927,976 A | 7/1999 | Wu | 433/82 |
| 5,928,238 A | 7/1999 | Scarborough et al. | 606/79 |

(56) References Cited

U.S. PATENT DOCUMENTS

| | | |
|---|---|---|
| 5,941,706 A | 8/1999 | Ura .................... 433/165 |
| 5,941,851 A | 8/1999 | Coffey et al. .................. 604/131 |
| 5,951,026 A | 9/1999 | Harman, Jr. et al. .......... 279/143 |
| 5,960,797 A * | 10/1999 | Kramer et al. ................ 128/899 |
| 5,980,545 A | 11/1999 | Pacala et al. ................. 606/170 |
| 5,993,417 A | 11/1999 | Yerfino et al. ................ 604/110 |
| 5,993,454 A | 11/1999 | Longo ............................. 606/80 |
| 6,007,496 A | 12/1999 | Brannon ....................... 600/565 |
| 6,017,348 A | 1/2000 | Hart et al. ....................... 606/79 |
| 6,018,094 A | 1/2000 | Fox ................................ 623/11 |
| 6,022,324 A | 2/2000 | Skinner ......................... 600/566 |
| 6,027,458 A | 2/2000 | Janssens ....................... 600/567 |
| 6,033,369 A | 3/2000 | Goldenberg ................... 600/567 |
| 6,033,411 A | 3/2000 | Preissman ....................... 606/99 |
| 6,063,037 A | 5/2000 | Mittermeier et al. .......... 600/567 |
| 6,071,284 A | 6/2000 | Fox ................................. 606/80 |
| 6,080,115 A | 6/2000 | Rubinstein .................... 600/567 |
| 6,083,176 A | 7/2000 | Terwilliger .................... 600/562 |
| 6,086,544 A | 7/2000 | Hibner et al. ................. 600/568 |
| 6,096,042 A | 8/2000 | Herbert ........................... 606/80 |
| 6,102,915 A | 8/2000 | Bresler et al. ................... 606/80 |
| 6,106,484 A | 8/2000 | Terwilliger .................... 600/568 |
| 6,110,128 A | 8/2000 | Andelin et al. ............... 600/566 |
| 6,110,129 A | 8/2000 | Terwilliger .................... 600/567 |
| 6,110,174 A | 8/2000 | Nichter ........................... 606/72 |
| 6,120,462 A | 9/2000 | Hibner et al. ................. 600/566 |
| 6,135,769 A | 10/2000 | Kwan ............................. 433/80 |
| 6,152,918 A | 11/2000 | Padilla et al. ................... 606/15 |
| 6,159,163 A | 12/2000 | Strauss et al. ................ 600/566 |
| 6,162,203 A | 12/2000 | Haaga ........................... 604/272 |
| 6,183,442 B1 | 2/2001 | Athanasiou et al. .......... 604/154 |
| 6,210,376 B1 | 4/2001 | Grayson ........................ 604/264 |
| 6,217,561 B1 | 4/2001 | Gibbs ............................ 604/264 |
| 6,221,029 B1 | 4/2001 | Mathis et al. ................. 600/564 |
| 6,228,049 B1 | 5/2001 | Schroeder et al. .......... 604/93.01 |
| 6,228,088 B1 | 5/2001 | Miller et al. .................... 606/80 |
| 6,238,355 B1 | 5/2001 | Daum ........................... 600/567 |
| 6,247,928 B1 | 6/2001 | Meller et al. .................... 433/80 |
| 6,248,110 B1 | 6/2001 | Reiley et al. ................... 606/93 |
| 6,257,351 B1 | 7/2001 | Ark et al. ...................... 173/178 |
| 6,267,763 B1 | 7/2001 | Castro ........................ 606/86 A |
| 6,273,715 B1 | 8/2001 | Meller et al. .................... 433/80 |
| 6,273,862 B1 | 8/2001 | Privitera et al. ............... 600/568 |
| 6,283,925 B1 | 9/2001 | Terwilliger .................... 600/568 |
| 6,283,970 B1 | 9/2001 | Lubinus .......................... 606/80 |
| 6,287,114 B1 | 9/2001 | Meller et al. .................... 433/80 |
| 6,302,852 B1 | 10/2001 | Fleming, III et al. ......... 600/567 |
| 6,309,358 B1 | 10/2001 | Okubo ........................... 600/466 |
| 6,312,394 B1 | 11/2001 | Fleming, III .................. 600/567 |
| 6,315,737 B1 | 11/2001 | Skinner ......................... 600/566 |
| 6,325,806 B1 | 12/2001 | Fox ................................. 606/80 |
| 6,328,701 B1 | 12/2001 | Terwilliger .................... 600/567 |
| 6,328,744 B1 | 12/2001 | Harari et al. .................... 606/80 |
| 6,358,252 B1 | 3/2002 | Shapira ........................... 606/80 |
| 6,382,212 B1 | 5/2002 | Borchard ...................... 128/849 |
| 6,402,701 B1 | 6/2002 | Kaplan et al. ................. 600/567 |
| 6,419,490 B1 | 7/2002 | Kitchings Weathers, Jr. 433/165 |
| 6,425,888 B1 | 7/2002 | Embleton et al. ............. 604/290 |
| 6,428,487 B1 | 8/2002 | Burdorff et al. .............. 600/568 |
| 6,443,910 B1 | 9/2002 | Krueger et al. ............... 600/567 |
| 6,468,248 B1 | 10/2002 | Gibbs ........................ 604/164.01 |
| 6,478,751 B1 | 11/2002 | Krueger et al. ............... 600/566 |
| 6,488,636 B2 | 12/2002 | Bryan et al. .................. 600/565 |
| 6,523,698 B1 | 2/2003 | Dennehey et al. ............ 210/435 |
| 6,527,736 B1 | 3/2003 | Attinger et al. ................. 604/43 |
| 6,527,778 B2 | 3/2003 | Athanasiou et al. ............ 606/80 |
| 6,540,694 B1 | 4/2003 | Van Bladel et al. ........... 600/564 |
| 6,547,511 B1 | 4/2003 | Adams ......................... 414/46.4 |
| 6,547,561 B2 | 4/2003 | Meller et al. .................... 433/80 |
| 6,550,786 B2 | 4/2003 | Gifford et al. .................. 279/75 |
| 6,554,779 B2 | 4/2003 | Viola et al. ................... 600/568 |
| 6,555,212 B2 | 4/2003 | Boiocchi et al. ............. 428/295.4 |
| 6,572,563 B2 | 6/2003 | Ouchi ........................... 600/564 |
| 6,575,919 B1 | 6/2003 | Reiley et al. ................. 600/567 |
| 6,582,399 B1 | 6/2003 | Smith et al. ................... 604/152 |
| 6,585,622 B1 | 7/2003 | Shum et al. ......................... 482/8 |
| 6,595,911 B2 | 7/2003 | LoVuolo .......................... 600/30 |
| 6,595,979 B1 | 7/2003 | Epstein et al. |
| 6,613,054 B2 | 9/2003 | Scribner et al. ................. 606/93 |
| 6,616,632 B2 | 9/2003 | Sharp et al. ................... 604/117 |
| 6,620,111 B2 | 9/2003 | Stephens et al. .............. 600/567 |
| 6,626,848 B2 | 9/2003 | Nueenfeldt ................... 600/564 |
| 6,626,887 B1 | 9/2003 | Wu ................................ 604/512 |
| 6,638,235 B2 | 10/2003 | Miller et al. ................... 600/566 |
| 6,656,133 B2 | 12/2003 | Voegele et al. ............... 600/568 |
| 6,689,072 B2 | 2/2004 | Kaplan et al. ................. 600/567 |
| 6,702,760 B2 | 3/2004 | Krause et al. ................. 600/564 |
| 6,702,761 B1 | 3/2004 | Damadian et al. ............ 600/576 |
| 6,706,016 B2 | 3/2004 | Cory et al. .................... 604/117 |
| 6,716,192 B1 | 4/2004 | Orosz, Jr. ...................... 604/117 |
| 6,716,215 B1 | 4/2004 | David et al. ..................... 606/80 |
| 6,716,216 B1 | 4/2004 | Boucher et al. ................. 606/86 |
| 6,730,043 B2 | 5/2004 | Krueger et al. ............... 600/567 |
| 6,730,044 B2 | 5/2004 | Stephens et al. .............. 600/568 |
| 6,749,576 B2 | 6/2004 | Bauer ............................ 600/567 |
| 6,752,768 B2 | 6/2004 | Burdoff et al. ................ 600/568 |
| 6,758,824 B1 | 7/2004 | Miller et al. ................... 600/568 |
| 6,761,726 B1 | 7/2004 | Findlay et al. ................ 606/182 |
| 6,796,957 B2 | 9/2004 | Carpenter et al. .......... 604/93.01 |
| 6,846,314 B2 | 1/2005 | Shapira ........................... 606/80 |
| 6,849,051 B2 | 2/2005 | Sramek et al. ................ 600/565 |
| 6,855,148 B2 | 2/2005 | Foley et al. ..................... 606/86 |
| 6,860,860 B2 | 3/2005 | Viola ............................. 600/564 |
| 6,875,183 B2 | 4/2005 | Cervi ............................ 600/567 |
| 6,875,219 B2 | 4/2005 | Arramon et al. ................ 606/92 |
| 6,884,245 B2 | 4/2005 | Spranza .......................... 606/79 |
| 6,887,209 B2 | 5/2005 | Kadziauskas et al. ......... 600/565 |
| 6,890,308 B2 | 5/2005 | Islam ............................ 600/564 |
| 6,905,486 B2 | 6/2005 | Gibbs ............................ 604/264 |
| 6,930,461 B2 | 8/2005 | Ruthowski .................... 318/567 |
| 6,942,669 B2 | 9/2005 | Kurc ............................... 606/80 |
| 6,969,373 B2 | 11/2005 | Schwartz et al. .......... 604/170.03 |
| 7,001,342 B2 | 2/2006 | Faciszewski .................. 600/564 |
| 7,008,381 B2 | 3/2006 | Janssens ....................... 600/564 |
| 7,008,383 B1 | 3/2006 | Damadian et al. ............ 600/567 |
| 7,008,394 B2 | 3/2006 | Geise et al. .................. 615/6.15 |
| 7,018,343 B2 | 3/2006 | Plishka ......................... 600/564 |
| 7,025,732 B2 | 4/2006 | Thompson et al. ........... 600/654 |
| 7,063,672 B2 | 6/2006 | Schramm ..................... 600/564 |
| 7,063,703 B2 | 6/2006 | Reo ................................ 606/79 |
| 7,137,985 B2 | 11/2006 | Jahng ............................. 606/61 |
| 7,186,257 B2 | 3/2007 | Kim ................................ 606/96 |
| 7,207,949 B2 | 4/2007 | Miles et al. ................... 600/554 |
| 7,226,450 B2 | 6/2007 | Athanasiou et al. ............ 606/80 |
| 7,229,401 B2 | 6/2007 | Kindlein ........................... 600/7 |
| 7,278,972 B2 | 10/2007 | Lamoureux et al. .......... 600/567 |
| 7,331,930 B2 | 2/2008 | Faciszewski .................. 600/567 |
| 7,513,722 B2 | 4/2009 | Greenberg et al. ........... 408/202 |
| 7,850,620 B2 | 12/2010 | Miller et al. ................... 600/568 |
| 7,951,089 B2 | 5/2011 | Miller ........................... 600/566 |
| 7,988,643 B2 | 8/2011 | Hoffmann et al. ............ 600/567 |
| 8,038,664 B2 | 10/2011 | Miller et al. ................... 604/506 |
| 8,419,683 B2 | 4/2013 | Miller et al. ................... 604/117 |
| 8,480,632 B2 | 7/2013 | Miller et al. ................... 604/188 |
| 8,506,568 B2 | 8/2013 | Miller ............................. 606/80 |
| 8,641,715 B2 | 2/2014 | Miller ............................. 606/80 |
| 8,656,929 B2 | 2/2014 | Miller et al. ................... 128/898 |
| 8,684,978 B2 | 4/2014 | Miller et al. ................... 604/235 |
| 8,690,791 B2 | 4/2014 | Miller ........................... 600/562 |
| 8,715,287 B2 | 5/2014 | Miller ............................. 606/80 |
| 2001/0014439 A1 | 8/2001 | Meller et al. .................... 433/50 |
| 2001/0047183 A1 | 11/2001 | Privitera et al. ............... 606/170 |
| 2001/0053888 A1 | 12/2001 | Athanasiou et al. .......... 604/154 |
| 2002/0042581 A1 | 4/2002 | Cervi ............................ 600/567 |
| 2002/0055713 A1 | 5/2002 | Gibbs ........................ 604/164.01 |
| 2002/0120212 A1 | 8/2002 | Ritchart et al. ............... 600/567 |
| 2002/0138021 A1 | 9/2002 | Pflueger ....................... 600/565 |
| 2003/0028146 A1 | 2/2003 | Aves ........................ 604/164.06 |
| 2003/0032939 A1 | 2/2003 | Gibbs ............................ 604/510 |
| 2003/0036747 A1 | 2/2003 | Ie et al. ............................. 606/1 |
| 2003/0050574 A1 | 3/2003 | Krueger ........................ 600/567 |
| 2003/0114858 A1 | 6/2003 | Athanasiou et al. ............ 606/80 |
| 2003/0125639 A1 | 7/2003 | Fisher et al. .................. 600/564 |
| 2003/0153842 A1 | 8/2003 | Lamoureux et al. .......... 600/564 |

(56) References Cited

U.S. PATENT DOCUMENTS

| | | | |
|---|---|---|---|
| 2003/0191414 A1 | 10/2003 | Reiley et al. | 600/567 |
| 2003/0195436 A1 | 10/2003 | Van Bladel et al. | 600/584 |
| 2003/0195524 A1 | 10/2003 | Barner | 606/119 |
| 2003/0199787 A1 | 10/2003 | Schwindt | 600/568 |
| 2003/0199879 A1 | 10/2003 | Spranza | 606/79 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | 606/80 |
| 2004/0019297 A1 | 1/2004 | Angel | 600/564 |
| 2004/0019299 A1 | 1/2004 | Richart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0073139 A1 | 4/2004 | Hirsch et al. | 600/564 |
| 2004/0092946 A1 | 5/2004 | Bagga et al. | 606/93 |
| 2004/0127814 A1 | 7/2004 | Negroni | 600/567 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | 600/562 |
| 2004/0220497 A1 | 11/2004 | Findlay et al. | 600/562 |
| 2005/0027210 A1 | 2/2005 | Miller | 600/567 |
| 2005/0040060 A1 | 2/2005 | Anderson et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller, Jr. et al. | 600/568 |
| 2005/0124915 A1 | 6/2005 | Eggers et al. | 600/568 |
| 2005/0131345 A1 | 6/2005 | Miller | 604/117 |
| 2005/0148940 A1* | 7/2005 | Miller | 604/187 |
| 2005/0165328 A1 | 7/2005 | Heske et al. | 600/566 |
| 2005/0165403 A1 | 7/2005 | Miller | 606/79 |
| 2005/0165404 A1 | 7/2005 | Miller | 606/80 |
| 2005/0171504 A1 | 8/2005 | Miller | 604/506 |
| 2005/0182394 A1 | 8/2005 | Spero et al. | 606/21 |
| 2005/0200087 A1 | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2005/0261693 A1 | 11/2005 | Miller et al. | 606/80 |
| 2006/0011506 A1 | 1/2006 | Riley | 206/570 |
| 2006/0015066 A1 | 1/2006 | Turieo et al. | 604/136 |
| 2006/0036212 A1 | 2/2006 | Miller | 604/48 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Richart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2007/0016100 A1 | 1/2007 | Miller | 600/567 |
| 2007/0049945 A1 | 3/2007 | Miller | 606/86 |
| 2007/0149920 A1 | 6/2007 | Michels et al. | 604/93.01 |
| 2007/0213735 A1 | 9/2007 | Saadat et al. | 606/79 |
| 2007/0270775 A1 | 11/2007 | Miller et al. | 604/506 |
| 2008/0015467 A1 | 1/2008 | Miller | 600/568 |
| 2008/0015468 A1 | 1/2008 | Miller | 600/568 |
| 2008/0045857 A1 | 2/2008 | Miller | 600/566 |
| 2008/0045860 A1 | 2/2008 | Miller et al. | 600/567 |
| 2008/0045861 A1 | 2/2008 | Miller et al. | 600/567 |
| 2008/0045965 A1 | 2/2008 | Miller et al. | 606/80 |
| 2008/0140014 A1 | 6/2008 | Miller et al. | 604/180 |
| 2008/0177200 A1 | 7/2008 | Ikehara et al. | 600/567 |
| 2008/0215056 A1 | 9/2008 | Miller et al. | 606/80 |
| 2008/0221580 A1 | 9/2008 | Miller et al. | 606/80 |

FOREIGN PATENT DOCUMENTS

| | | | |
|---|---|---|---|
| EP | 517000 | 12/1992 | |
| EP | 0 807 412 A1 | 11/1997 | A61B 17/32 |
| EP | 0807412 | 11/1997 | |
| EP | 1099450 | 5/2001 | A61M 5/32 |
| EP | 1314452 | 5/2003 | |
| EP | 1421907 | 5/2004 | |
| EP | 1447050 | 8/2004 | |
| FR | 853 349 | 3/1940 | |
| FR | 2 457 105 | 5/1979 | A61M 5/00 |
| FR | 2 516 386 | 11/1981 | A61M 5/18 |
| GB | 2 130 890 A | 6/1984 | A61B 10/00 |
| JP | 59119808 | 8/1984 | |
| JP | 6132663 | 9/1986 | |
| WO | WO 92/08410 | 5/1992 | |
| WO | 93/07819 | 4/1993 | A61B 17/32 |
| WO | 96/31164 | 10/1996 | A61B 17/34 |
| WO | 98/06337 | 2/1998 | A61B 17/16 |
| WO | WO 98/52638 | 11/1998 | |
| WO | 99/18866 | 4/1999 | A61B 17/34 |
| WO | 99/52444 | 10/1999 | A61B 17/00 |
| WO | WO 00/09024 | 2/2000 | |
| WO | 00/56220 | 9/2000 | A61B 10/00 |
| WO | 02/41792 A1 | 5/2002 | A61B 17/16 |
| WO | 2417921 | 5/2002 | A61B 17/16 |
| WO | 02096497 | 12/2002 | A61M 31/00 |
| WO | WO 03/015637 | 2/2003 | |
| WO | WO 2005/072625 | 8/2005 | |
| WO | 2005110259 | 11/2005 | |
| WO | 2005/112800 | 12/2005 | A61B 17/34 |
| WO | 2005112800 | 12/2005 | A61B 17/34 |
| WO | 2008081438 | 7/2008 | |

OTHER PUBLICATIONS

Official Action for European Application No. 03756317.8 (4 pages), Dec. 28, 2006.

International Search Report and Written Opinion for International Application No. PCT/US2006/025201 (18 pages), Jan. 29, 2007.

Australian Exam Report on Patent Application No. 2003240970, 2 pages, Oct. 15, 2007.

Pediatric Emergency, Intraosseous Infusion for Administration of Fluids and Drugs, www.cookgroup.com, 1 pg, 2000.

Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages, 2008.

Buckley et al., CT-guided bone biopsy: Initial experience with commercially available hand held Black and Decker drill, European Journal of Radiology 61, pp. 176-180, 2007.

Hakan et al., CT-guided Bone BiopsyPerformed by Means of Coaxial Bopsy System with an Eccentric Drill, Radiology, pp. 549-552, Aug. 1993.

European Search Report 08158699.2-1265, 4 pages, Aug. 2008.

International Search Report and Written Opinion, PCT/US2007/078204, 14 pages, Mailing Date May 15, 2008.

International Search Report and Written Opinion, PCT/US08/52943, 8 pages, Mailing Date Sep. 26, 2008.

European Office Action Communication, Application No. 08158699.2-1265/1967142, 10 pages, Nov. 4, 2008.

BioAccess.com, Single Use Small Bone Power Tool—How It Works, 1 pg, Printed Jun. 9, 2008.

International Search Report and Written Opinion, PCT/US2007/078203, 15 pages, Mailing Date May 13, 2008.

International Search Report and Written Opinion, PCT/US2007/072202, 17 pages, Mailing Date Mar. 25, 2008.

International Search Report and Written Opinion, PCT/US2007/078207, 13 pages, Mailing Date Apr. 7, 2008.

International Search Report and Written Opinion, PCT/US2007/078205, 13 pages, Mailing date Sep. 11, 2007.

(56) References Cited

OTHER PUBLICATIONS

European Office Action EP03731475.4, 4 pages, Oct. 11, 2007.
U.S. Appl. No. 11/427,501 Non Final Office Action, 14 pages, Mailed Aug. 7, 2008.
PCT Preliminary Report on Patentability, PCT/US/2008/050346, (8 pgs), Jul. 23, 2009.
Liakat A. Parapia, Trepanning or trephines: a history of bone marrow biopsy, British Journal of Haematology, pp. 14-19, 2007.
Chinese Office Action with English translation; Application No. 200880000022.0; pp. 10, Dec. 13, 2010.
International Search Report, PCT/US2007/072209, 9 pages, Mailing Date Mar. 12, 2007.
International Search Report, PCT/US2007/072217, 9 pages, Mailing Date Mar. 12, 2007.
"Proven reliability for quality bone marrow samples", Special Procedures, Cardinal Health, 6 pages, 2003.
F.A.S.T. 1 Intraosseous Infusion System with Depth-Control Mechanism Brochure, 6 pages, 2000.
Åström, K.G., "Automatic Biopsy Instruments Used Through a Coaxial Bone Biopsy System with an Eccentric Drill Tip," Acta Radiologica, 1995; 36:237-242, May 1995.
Åström, K. Gunnar O., "CT-guided Transsternal Core Biopsy of Anterior Mediastinal Masses," Radiology 1996; 199:564-567, May 1996.
International Preliminary Report on Patentability, PCT/US2007/072202, 10 pages, Mailed Jan. 15, 2009.
International Preliminary Report on Patentability, PCT/US2007/072217, 11 pages, Mailed Feb. 12, 2009.
PCT Invitation to Pay Additional Fees, PCT/US2007/072209, 9 pages, Mailing Dec. 3, 2007.
Non-Final Office Action mailed Mar. 23, 2009 and Response to Office Action filed Jun. 22, 2009, U.S. Appl. No. 11/190,331, 61 pages, Mar. 23, 2009.
International Preliminary Report on Patentability, PCT/US/2007/078203, 13 pages, Mar. 26, 2009.
International Preliminary Report on Patentability, PCT/US/2007/078207, 10 pages, Mar. 26, 2009.
International Preliminary Report on Patentability, PCT/US/2007/078205, 10 pages, Mar. 26, 2009.
International Preliminary Report on Patentability, PCT/US/2007/078204, 11 pages, Apr. 2, 2009.
Non-Final Office Action mailed Apr. 1, 2009 and Response to Office Action filed Jul. 1, 2009, U.S. Appl. No. 10/449,503, 48 pages, Apr. 1, 2009.
Vidacare Corporation Comments to Intraosseous Vascular Access Position Paper, Infusion Nurses Society, 6 pages, May 4, 2009.
Non-Final Office Action mailed May 13, 2009 and Response to Office Action filed Jul. 1, 2009, U.S. Appl. No. 11/427,501, 30 pages, May 13, 2009.
International Preliminary Report on Patentability, PCT/US/2007/072209, 10 pages, May 14, 2009.
Non-Final Office Action mailed 05/29/09 and Response to Office Action filed Aug. 12, 2009 U.S. Appl. No. 10/449,476, 20 pages, May 29, 2009.
Final Office Action, U.S. Appl. No. 11/781,568 and Request for Continued Examination and Amendment filed Sep. 17, 2009, 46 pages, Jun. 17, 2009.
Final Office Action, U.S. Appl. No. 11/064,156, (12 pages) and Request for Continued Examination and Amendment filed Nov. 19, 2009, 22 pages. (34 pages TOTAL), Jun. 19, 2009.
Final Office Action, U.S. Appl. No. 11/853,685, 21 pages, Jun. 24, 2009.
Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org, Feb. 21, 2007.
International Search Report for International Application No. PCT/US03/17167 (8 pages), Sep. 16, 2003.
International Search Report for International Application No. PCT/US03/17203 (8 pages), Sep. 16, 2003.
International Search Report for International Application No. PCT/US2004/037753 (6 pages), Apr. 19, 2005.
Communication relating to the results of the partial International Search Report for International Application No. PCT/US2005/002484 (6 pages), May 19, 2005.
Cummins et al. "ACLS-Principles and Practice," ACLS-The Reference Textbook, American Heart Association (pp. 214-218), 2003.
Riley et al. "A Pathologist's Perspective on Bone Marrow Aspiration Biopsy: I. Performing a Bone Marrow Examination" Journal of Clinical Laboratory Analysis 18 (pp. 70-90) 2004.
U.S. Patent Application Publication No. US 2002/0138021 dated Sep. 26, 2002 for U.S. Appl. No. 10/093,775, filed Mar. 8, 2002 (now abandoned).
International Preliminary Report on Patentability for International Application No. PCT/US2005/002484 (9 pages), Aug. 3, 2006.
International Search Report and Written Opinion for International Application No. PCT/US2004/037753 (16 pages), Jul. 8, 2005.
International Search Report and Written Opinion for International Application No. PCT/US2005/002484 (15 pages), Jul. 22, 2005.
European Office Action; Application No. 09 155 111.9-2310; pp. 3, Nov. 25, 2009.
Chinese Office Action with English translation; Application No. 200910006631.3; pp. 12, Mar. 11, 2010.
European Extended Search Report, Application No. EP10153350.3, 5 pages, Mar. 11, 2010.
Gunal et al., Compartment Syndrome After Intraosseous Infusion: An Expiremental Study in Dogs, Journal of Pediatric Surgery, vol. 31, No. 11, pp. 1491-1493, Nov. 1996.
International Search Report, PCT/US2007/072217, 20 pages, Mailing Date Mar. 31, 2008.
International Search Report, PCT/US2007/072209, 18 pages, Mailing Date Apr. 25, 2008.
International Search Report, PCT/US2006/025201, 12 pages, Mailing Date Feb. 7, 2008.
Communication Pursuant to Article 94(3) EPC, Application No. 05 712 091.7-1265, 4 pages, Apr. 8, 2008.
Notification of the First Chinese Office Action, Application No. 200580003261.8, 3 pages, Mar. 21, 2008.
International Search Report and Written Opinion, PCT/US08/500346, 12 pages, Mailing Date May 22, 2008.
Extended European Search Report for European application 07842284.7. Mailed Mar. 16, 2011.
Extended European Search Report for European application 07842285.4. Mailed Mar. 17. 2011.
Extended European Search Report for European application 07842286.2. Mailed Mar. 18, 2011.
Extended European Search Report for European application 07842288.8. Mailed Mar. 16. 2011.
International Preliminary Report on Patentability for international application PCT/US2007/078205. Dated Mar. 17, 2009.
Office Communication issued in Taiwanese Patent Application No. 093134480, dated Jan. 15, 2011.
Notice of Allowance in U.S. Appl. No. 11/042,912, mailed Sep. 24, 2013.
Notice of Allowance in U.S. Appl. No. 11/853,678, mailed Oct. 11, 2013.
Notice of Allowance in U.S. Appl. No. 11/853,678, mailed Nov. 8, 2013.
Notice of Allowance in U.S. Appl. No. 12/899,696, mailed Nov. 12, 2013.
Notice of Allowance in U.S. Appl. No. 12/427,310, mailed Nov. 29, 2013.
Notice of Allowance in U.S. Appl. No. 12/331,979, mailed Dec. 23, 2013.
Notice of Allowance in U.S. Appl. No. 11/253,467, mailed Jun. 24, 2014.
Notice of Allowance in U.S. Appl. No. 11/253,959, mailed May 20, 2013.

* cited by examiner

INTRAOSSEOUS DEVICE AND METHODS FOR ACCESSING BONE MARROW IN THE STERNUM AND OTHER TARGET AREAS

RELATED APPLICATION

This application is a Continuation-in-Part Application claiming priority to U.S. patent application Ser. No. 10/987,051, filed Nov. 12, 2004, and entitled "Apparatus and Method for Accessing the Bone Marrow of the Sternum."

TECHNICAL FIELD

The present disclosure is related to apparatus and methods to accessing bone marrow at various target areas including, but not limited to, a patient's sternum.

BACKGROUND OF THE DISCLOSURE

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. According to the American Heart Association, more than 1,500,000 patients suffer from heart attacks (myocardial infarctions) every year, with over 500,000 of them dying from its devastating complications. Many wounded soldiers die within an hour of injury, usually from severe bleeding and/or shock. Many of these soldiers die unnecessarily because intravenous (IV) access cannot be achieved in a timely manner.

An essential element for treating many life threatening emergencies is rapid establishment of an IV line in order to administer drugs and fluids directly into a patient's vascular system. Whether in an ambulance by paramedics, in an emergency room by emergency specialists or on a battlefield by an Army medic, the goal is the same—quickly start an IV in order to administer lifesaving drugs and fluids. To a large degree, ability to successfully treat most critical emergencies is dependent on the skill and luck of an operator in accomplishing vascular access. While relatively easy to start an IV on some patients, doctors, nurses and paramedics often experience great difficulty establishing IV access in approximately twenty percent of patients. The success rate on the battlefield may be much lower. Sometimes Army medics are only about twenty-nine percent successful in starting an IV line during battlefield conditions. These patients are often probed repeatedly with sharp needles in an attempt to solve this problem and may require an invasive procedure to finally establish intravenous access.

In the case of patients with chronic disease or the elderly, availability of easily accessible veins may be depleted. Other patients may have no available IV sites due to anatomical scarcity of peripheral veins, obesity, extreme dehydration or previous IV drug use. For such patients, finding a suitable site for administering lifesaving therapy often becomes a monumental and frustrating task. While morbidity and mortality statistics are not generally available, it is generally known that many patients with life threatening emergencies have died because access to the vascular system with lifesaving IV therapy was delayed or simply not possible.

The intraosseous (IO) space provides a direct conduit to a patient's vascular system and provides an attractive alternate route to administer IV drugs and fluids. Intraosseous infusion has long been the standard of care in pediatric emergencies when rapid IV access is not possible. The U.S. military used hand driven IO needles for infusions extensively and successfully during World War II. However, such IO needles were cumbersome, difficult to use, and often had to be manually driven into a bone.

Drugs administered intraosseously enter a patient's blood circulation system as rapidly as they do when given intravenously. In essence, bone marrow may function as a large non-collapsible vein.

SUMMARY OF THE DISCLOSURE

In accordance with teachings of the present disclosure, apparatus and methods to access bone marrow at various target areas such as a human sternum are provided. The apparatus and methods may include, but are not limited to, guide mechanism and/or templates to position an intraosseous device at a selected insertion site and to control depth of penetration into associated bone marrow. For some embodiments, such apparatus may include an intraosseous (IO) device operable to penetrate the sternum, a driver operable to insert the IO device into the sternum, and a depth control mechanism operable to limit depth of penetration of the IO device into the sternum. The IO device may include an outer cannula and an inner trocar. The IO device may also include a soft tissue penetrator and a fluid connector such as a Luer lock connection. The depth control mechanism may include a removable collar or a collar permanently attached to portions of the IO device.

The present disclosure may provide for some applications a manual driver, an IO needle set, a guide to position the IO needle set at an injection site and/or a depth control mechanism to limit depth of penetration of the IO needle set into bone marrow in a sternum.

Various aspects of the present disclosure may be described with respect to providing IO access at selected sites in a patient's sternum. The upper tibia proximate a patient's knee may be used as an insertion site for an IO device to establish access with a patient's vascular system in accordance with teachings of the present disclosure. The humerus in a patient's arm may also be used as an insertion site for IO access to a patient's vascular system in accordance with teachings of the present disclosure.

For some applications a removable guide and/or depth control mechanism may be provided to allow a relatively long intraosseous device appropriate for insertion at a tibia or humerus to also be satisfactorily inserted into a sternum. Typically intraosseous devices used to access sternal bone marrow are relatively short as compared to intraosseous devices used to access bone marrow proximate a tibia or humerus.

Insertion sites and target areas for successful placement of an IO device in a patient's sternum may be larger than target areas for placement of IV devices. However, the use of guide mechanisms and/or depth control mechanisms incorporating teachings of present disclosure may be desired when an IO device is inserted in close proximity to a patient's heart, lungs and associated blood vessels. Guide mechanisms, depth control mechanisms and various techniques incorporating teachings of the present disclosure may substantially reduce and/or eliminate potential problems associated with inserting an intraosseous device into a patient's sternum during difficult emergency conditions and/or field operating environments.

One aspect of the present disclosure may be a method of establishing access to an intraosseous space or target area including contacting skin and other soft tissue covering an insertion site with a scalpel or blade to form an incision in the skin and other soft tissue. Apparatus including a driver, an IO needle set and a depth control mechanism may be used to provide access to an intraosseous space or target area adjacent to the insertion site. Portions of the IO needle set and the depth control mechanism may be inserted into the incision. The driver may then be used to insert portions of the IO needle set to a desired depth in the intraosseous space or target area. For some applications a manual driver may be releasably engaged with an IO needle set incorporating teachings of the present disclosure. For other applications a manual driver may be permanently attached to or formed as an integral component of a portion of the IO needle set.

Teachings of the present disclosure are not limited to providing IO access in a sternum. Various teachings of the present disclosure may be used to provide IO access to other target areas and may also be used during treatment of animals in a veterinary practice.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein.

DETAILED DESCRIPTION OF THE DISCLOSURE

Figure 1:
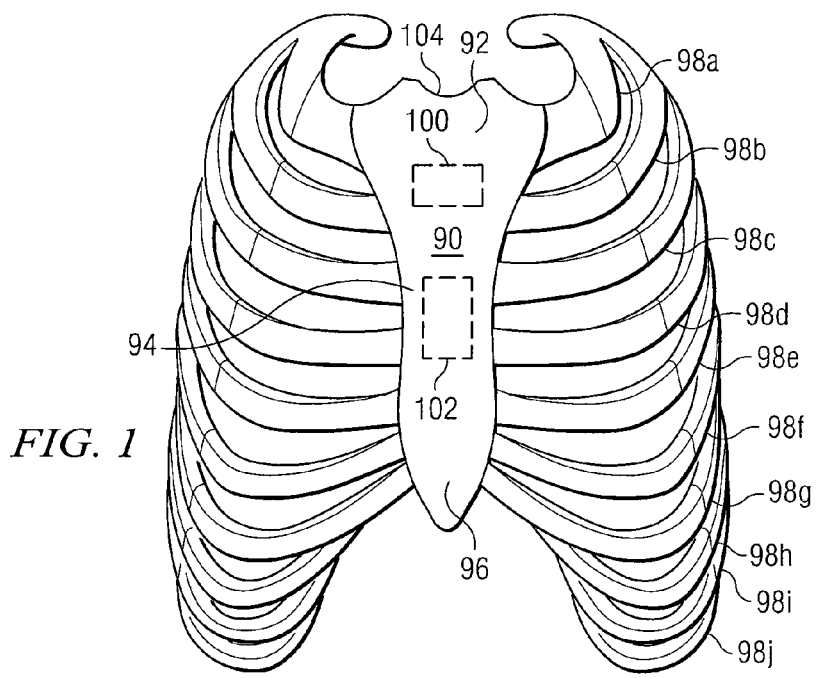
FIG. 1 is a schematic drawing showing portions of a human sternum and attached ribs.

Some preferred embodiments of the disclosure and associated advantages may be best understood by reference to FIGS. 1-8C wherein like numbers refer to same and like parts.

Vascular system access may be essential for treatment of many serious diseases, chronic conditions and acute emergency situations. Yet, many patients experience extreme difficulty obtaining effective treatment because of inability to obtain or maintain intravenous (IV) access. An intraosseous (IO) space provides a direct conduit to a patent's vascular system and systemic circulation. Therefore, IO access is an effective route to administer a wide variety of drugs, other medications and fluids. Rapid IO access offers great promise for almost any serious emergency that requires vascular access to administer life saving drugs, other medications and/or fluids when traditional IV access is difficult or impossible.

An intraosseous space may generally be described as region where cancellous bone and associated medullary cavity combine. Bone marrow typically includes blood, blood forming cells, and connective tissue found in an intraosseous space surrounded by compact bone. For purposes of illustration, compact bone disposed nearer the anterior or dorsal surface shall be referred to as "anterior compact bone" or "anterior bone cortex." Compact bone disposed farther from the dorsal or anterior surface may be referred to as "posterior compact bone" or "posterior bone cortex."

IO access may be used as a "bridge" (temporary fluid and drug therapy) during emergency conditions until conventional IV sites can be found and used. Conventional IV sites often become available because fluids and/or medication provided via IO access may stabilize a patient and expand veins and other portions of a patient's vascular system. IO devices and associated procedures incorporating teachings of the present disclosure may become standard care for administering medications and fluids in situations when IV access is difficult or not possible.

Intraosseous access may be used as a "routine" procedure with chronic conditions which substantially reduce or eliminate availability of conventional IV sites. Examples of such chronic conditions may include, but are not limited to, dialysis patients, patients in intensive care units and epilepsy patients. Intraosseous devices and associated apparatus incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description.

The term "driver" may be used in this application to include any type of power driver or manual driver satisfactory for inserting an intraosseous (IO) device such as a penetrator assembly or an IO needle into selected portions of a patient's vascular system. Various techniques may be satisfactorily used to releasably engage or attach an IO device and/or penetrator assembly with manual drivers and power drivers.

For some applications a manual driver may be securely attached to a portion of an IO device or may be formed as an integral component of an IO device. For some applications a power driver or a manual driver may be directly coupled with an IO device. Various types of connectors may also be used to releasably couple a manual driver or a power driver with an IO device. A wide variety of connectors and associated connector receptacles, fittings and/or other types of connections with various dimensions and configurations may be satisfactorily used to engage an IO device with a power driver or a manual driver.

The term "intraosseous (IO) device" may be used in this application to include any hollow needle, hollow drill bit, penetrator assembly, bone penetrator, catheter, cannula, trocar, inner penetrator, outer penetrator, IO needle or IO needle set operable to provide access to an intraosseous space or interior portions of a bone. A wide variety of trocars, spindles and/or shafts may be disposed within a cannula during insertion at a selected insertion site. Such trocars, spindles and shafts may also be characterized as inner penetrators. A catheter, cannula, hollow needle or hollow drill bit may sometimes be characterized as an outer penetrator.

For some applications a layer or coating (not expressly shown) of an anticoagulant such as, but not limited to, heparin may be placed on interior and/or exterior portions of a catheter or cannula to prevent thrombotic occlusion of the catheter or cannula. Anticoagulants may reduce platelet adhesion to interior surfaces of the catheter or cannula and may reduce clotting time of blood flowing into and through the catheter or cannula. Placing a layer of an anticoagulant on the exterior of a catheter or cannula adjacent to an associated tip may be helpful to prevent clotting.

The term "fluid" may be used in this application to describe any liquid including, but not limited to, blood, water, saline solutions, IV solutions, plasma or any mixture of liquids, particulate matter, dissolved medication and/or drugs appropriate for injection into bone marrow or other insertion sites. The term "fluid" may also be used within this patent application to include body fluids such as, but not limited to, blood and cells which may be withdrawn from a insertion site.

Various features of the present disclosure may be described with respect to manual drivers 20, 20a and 20d. Various features of the present disclosure may also be described with respect to intraosseous devices 160, 160a and 160b. However, guide and/or depth control mechanisms and insertion techniques incorporating teachings of the present disclosure may be satisfactorily used with a wide variety of drivers and intraosseous devices. The present disclosure is not limited to use with intraosseous devices 160, 160a, 160b, 160c or 160d or drivers 20, 20a, or 20d.

Power driver (not expressly shown) may include a housing with various types of motors and/or gear assemblies disposed therein. A rotatable shaft (not expressly shown) may be disposed within the housing and connected with a gear assembly (not expressly shown). Various types of fittings, connections, connectors and/or connector receptacles may be provided at one end of the rotatable shaft extending from a-power driver for releasable engagement with an IO device.

Examples of power drivers are shown in pending patent applications Ser. No. 10/449,503 filed May 30, 2003 entitled "Apparatus and Method to Provide Emergency Access To Bone Marrow," now U.S. Pat. No. 7,670,328; Ser. No. 10/449,476 filed May 30, 2003 entitled "Apparatus and Method to Access Bone Marrow," now U.S. Pat. No. 7,699,850; and Ser. No. 11/042,912 filed Jan. 25, 2005 entitled "Manual Intraosseous Device," now U.S. Pat. No. 8,641,715.

FIG. 1 shows portions of a bone structure associated with a human sternum. The bone structure shown in FIG. 1 may sometimes be referred to as the sternocostal region. Sternum 90 and associated pairs or sets of ribs 98a-98j form portions of a human rib cage. Sternum 90 as shown in FIG. 1 may be generally described as a flat, dagger-shaped bone. Sternum 90 may also be described as having three segments, manubrium 92, gladiolus 94, and xiphoid process 96.

Manubrium 92, connected to gladiolus 94, may sometimes be referred to as "the handle." Gladiolus 94 may sometimes be referred to as the body or "blade" of sternum 90. Xiphoid process 96 may be referred to as "the tip" of sternum 90. Xiphoid process 96 may be initially formed from cartilage but generally becomes boney in later years. Manubrium 92, gladiolus 94 and xiphoid process 96 are generally fused with each other in adults.

Two pairs or sets of ribs 98a and 98b may be attached to manubrium 92. Gladiolus 94 may be connected directly to third through seventh pairs or sets of ribs 98c-98i and indirectly to eighth pair or set of ribs 98j. Floating ribs are not shown in FIG. 1.

Sternum 90 may include insertion site 100 in manubrium 92 and insertion site 102 in gladiolus 94 for accessing bone marrow disposed therein. See FIGS. 3C, 4, 5A, 5B and 8C. Sternal notch 104 formed in manubrium 92 may be used with a guide mechanism incorporating teachings of the present disclosure to position an intraosseous device for insertion at insertion site 100 or 102.

Apparatus incorporating teachings of the present disclosure may include a driver operable to insert at least a portion of an IO device into an intraosseous space. Guide mechanisms and/or depth control mechanisms incorporating teachings of the present disclosure may also be provided when the IO device is inserted into a sternum or other target areas with limited space for penetration by the IO device. Examples of such mechanisms may include, but are not limited to, collar 170 shown in FIGS. 2A and 2B, collar 170a shown in FIG. 3B, guide 40 shown in FIGS. 3A and 3C, collar 170b shown in FIGS. 4, 5A and 5B and combined guide and depth control mechanism 60 with collar 62 shown in FIGS. 7, 8A, 8B and 8C. Combined guide and depth control mechanisms may sometimes be referred to as removable collars.

Figure 2A:
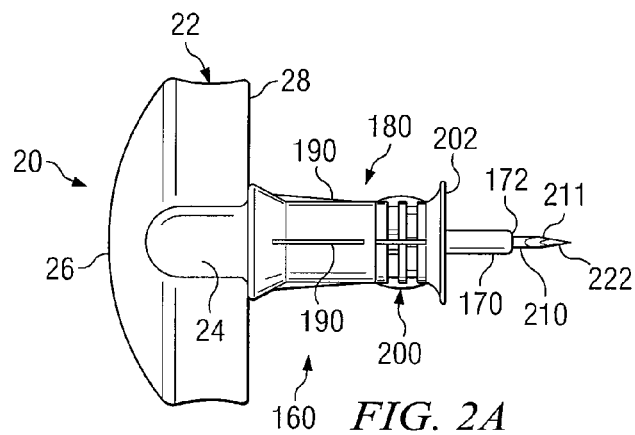
FIG. 2A is a schematic drawing showing apparatus operable to access bone marrow in accordance with teachings of the present disclosure.
Figure 2B:
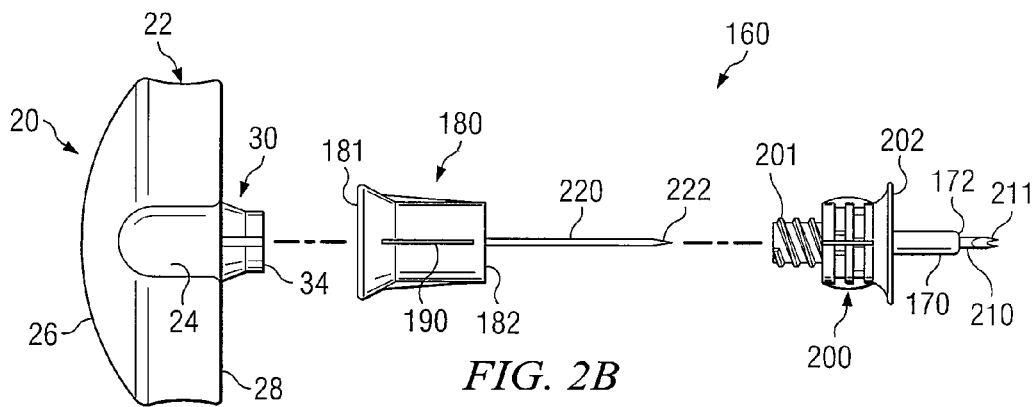
FIG. 2B is a schematic drawing showing an exploded view of the apparatus shown in FIG. 2A.
Figure 2C:
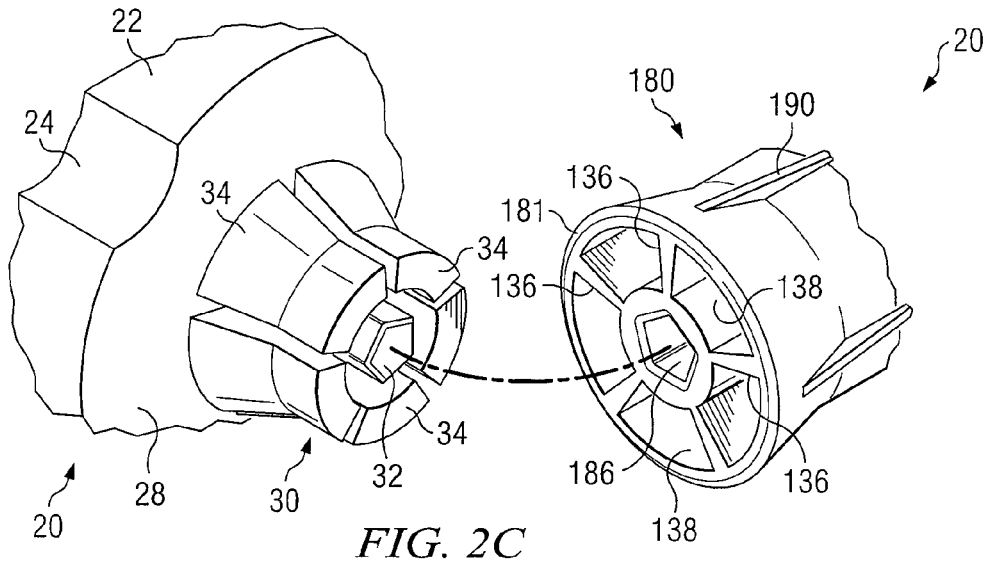
FIG. 2C is a schematic drawing showing an exploded, isometric view with portions broken away of one example of connectors operable to releasably engage a driver with an intraosseous device.

FIGS. 2A, 2B and 2C show one example of a manual driver and associated intraosseous device which may be used to provide vascular access in accordance with teachings of the present disclosure. Manual driver 20 may include handle 22 with a plurality of finger grips or finger rests 24 formed in the exterior thereof. Handle 22 may have a generally dome shaped configuration compatible with engagement by the palm (not expressly shown) of an operator's hand (not expressly shown). Dome shaped portion 26 of handle 22 and finger grips or finger rests 24 may have ergonically satisfactory designs.

As shown in FIGS. 2B and 2C connector 30 may extend from surface 28 of handle 22 opposite from dome shaped portion 26. Connector 30 may include drive shaft 32 extending therefrom. See FIG. 2C. Connector 30 may also include a plurality of tapered cylindrical segments 34 extending from surface 28 of handle 22 opposite from dome shaped portion 26. Each segment 34 may be sized to fit within corresponding void space or opening 138 formed in first end 181 of connector 180.

For embodiments such as shown in FIGS. 2A, 2B, 2C, 6A, 6B and 6C, intraosseous device or penetrator assembly 160 may include connector 180, associated hub 200, outer penetrator 210 and inner penetrator 220. Penetrator assembly 160 may include an outer penetrator such as a cannula, hollow tube or hollow drill bit and an inner penetrator such as a stylet or trocar. Various types of stylets and/or trocars may be disposed within an outer penetrator.

For some applications connector 180 may be described as having a generally cylindrical configuration defined in part by first end 181 and second end 182. SEE FIG. 2B. Exterior portions of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. See FIG. 2A. Longitudinal ridges 190 also allow connector 180 to be grasped for disengagement from hub 200 when outer penetrator 210 has been inserted into a bone and associated bone marrow.

First end 181 of connector of 180 may included opening 186 sized to receive portions drive shaft 32 therein. A plurality of webs 136 may extend radiantly outward from connector receptacle 186. Webs 136 cooperate with each other to form a plurality of openings 138 adjacent to first end 181. Opening 186 and openings 138 cooperate with each other to form portions of a connector receptacle operable to receive respective portions of connector 30 therein.

Second end 182 of connector 180 may include an opening (not expressly shown) sized to receive first end 201 of hub 200, 200a or 200b therein. Threads (not expressly shown) may be formed in the opening adjacent to second end 182 of connector 180. Such threads may be used to releasably attach connector 180 with threads 208 disposed adjacent to first end 201 of hubs 200, 200a and 200b. See FIGS. 4, 5A and 5B.

Respective first end 201 of hub 200 may have a generally cylindrical pin type configuration compatible with releasable engagement with second end or box end 182 of connector 180. For some applications first end 201 and threads 208 may provide portion of a Luer lock connection. Various types of Luer lock connections may be formed on first end 201 of hub 200 for use in to releasably engage tubing and/or other medical devices (not expressly shown) with hub 200 after intraosseous device 160 had been inserted into bone marrow at a target area and inner penetrator 220 removed from outer penetrator 210.

Metal disc 158 may be disposed within opening 186 for use in releasably attaching connector 180 with a magnetic drive shaft. See FIGS. 3C and 8C. For some applications, drive shaft 32 may be magnetized. End 223 of inner penetrator 220 may be spaced from metal disc 158 with insulating or electrically nonconductive material disposed there between.

For some applications outer penetrator or cannula 210 may be described as a generally elongated tube sized to receive inner penetrator or stylet 220 therein. Portions of inner penetrator 220 may be slidably disposed within a longitudinal passageway (not expressly shown) extending through outer penetrator 210. The outside diameter of inner penetrator 220 and the inside diameter of the longitudinal passageway may be selected such that inner penetrator 220 may be slidably disposed within outer penetrator 210.

Tip 211 of outer penetrator 210 and/or tip 222 of inner penetrator 220 may be operable to penetrate bone and associated bone marrow. The configuration of tips 211 and/or 222 may be selected to penetrate a bone or other body cavities with minimal trauma. First end or tip 222 of inner penetrator 220 may be trapezoid shaped and may include one or more cutting surfaces. In one embodiment outer penetrator 210 and inner penetrator 220 may be ground together as one unit during an associated manufacturing process. Providing a matching fit allows respective tips 211 and 222 to act as a single drilling unit which facilitates insertion and minimizes damage as portions of penetrator assembly 160 are inserted into a bone and associated bone marrow.

Inner penetrator 220 may also include a longitudinal groove (not expressly shown) that runs along the side of inner penetrator 220 to allow bone chips and/or tissues to exit an insertion site as penetrator assembly 160 is drilled deeper into an associated bone. Outer penetrator 210 and inner penetrator 220 may be formed from stainless steel, titanium or other materials of suitable strength and durability to penetrate bone.

For some applications a depth control mechanism incorporating teachings of the present disclosure, such as collar 170, may be disposed on and engaged with exterior portions of outer penetrator 210. For other applications a depth control mechanism such as collar 170a and exterior portions of outer penetrator 210 may be operable to rotate relative to each other. For still other applications a depth control mechanism such as collar 170b may be formed as part of associated hub 200a or 200b. See FIGS. 4, 5A AND 5B. For still further applications a removable depth control mechanism such as collar 62 may be used. See FIGS. 7, 8B and 8C. Collars 170, 170a, 170b and 62 may sometimes be referred to as "depth control limiters."

For some embodiments collar 170 may have a generally elongated, hollow configuration compatible with engaging the outside diameter of outer penetrator 210. One end of collar 170 (not expressly shown) may be installed over exterior portions of outer penetrator 210 and disposed within adjacent portions of hub 200. Second end 172 of collar 170 may extend a selected distance from flange 202 of hub 200. Various techniques such as, but not limited to, press fitting may be used to install collar 170 on exterior portions of outer penetrator 210.

The resulting spacing between second end 202 of hub 200 and second end 172 of collar 170 may limit depth of penetration of outer penetrator 210 into bone and associated bone marrow. Second end 202 of hub 200 and second end 172 of collar 170 may cooperate with each other to provide a depth limiting mechanism for associated intraosseous device or penetrator assembly 160. Collar 170 may be formed from various materials including stainless steel, titanium or other materials used to form outer penetrator 210.

Collar 170 will generally be securely engaged with the exterior of outer penetrator 210. As a result outer penetrator 210 and collar 170 will generally rotate with each other in response to rotation of manual driver 20. For other applications portions of an intraosseous device and an associated depth control mechanism may be operable to rotate relative to each other during insertion of the intraosseous device into bone marrow adjacent to a selected insertion site. See for example FIG. 3C.

Hubs 200, 200a and 200b may be used to stabilize respective penetrator assemblies 160 and 160b during insertion of an associated penetrator into a patient's skin, soft tissue and adjacent bone at a selected insertion site. SEE FIGS. 4, 5A and 5B. Hubs 200, 200a and 200b may also be used as a handle to manipulate outer penetrator 210 or remove outer penetrator 210 from a target area. Respective first end 201 of hub 200 and 200b may be operable for releasable engagement or attachment with associated connector 180.

Passageway 206 may extend from first end 201 through second end 202. SEE FIGS. 4, 5A AND 5B. The inside diameter of passageway 206 may be selected to securely engage the outside diameter of penetrator 210. The dimensions and configuration of passageway 206 may be selected to maintain associated outer penetrator 210 engaged with hub 200.

Second end 202 of hubs 200, 200a and 200b may have a size and configuration compatible with an insertion site for an associated penetrator assembly. The combination of hub 200 with outer penetrator 210 and inner penetrator 220 may sometimes be referred to as a "penetrator set" or "intraosseous needle set".

For some applications end 202 of hubs 200, 200a and 200b may have the general configuration of a flange. An angular slot or groove sized to receive one end of protective cover 233 (See FIG. 5C) or needle cap 234 (See FIG. 5D) may be formed in end 202. For example, slot or groove 204 as shown in FIG. 8C may be used to releasably engage cover 234 with penetrator assembly 160. Cover 233 as shown in FIG. 5C may include an enlarged inside diameter compatible with the outside diameter of collar 170. Cap 234 as shown in FIG. 5D may have a smaller inside diameter compatible with the exterior of outer cannula 210.

Protective cover 233 may be described as a generally hollow tube with an inside diameter compatible with the outside diameter of collar 170. The length of protective cover 233 may be greater than the distance between end 202 of hub 200 and the extreme end of tip 211. For some applications protective cover 233 may be formed by cutting plastic tubing (not expressly shown) having an appropriate inside diameter into segments having a desired length.

Needle cap 234 may be described as a generally hollow tube having closed, rounded end 232. See FIG. 5D. Cover 234 may be disposed within associated slot 204 to protect portions of outer penetrator 210 and inner penetrator 220 prior to attachment with an associated driver. Cover 234 may include a plurality of longitudinal ridges 236 which cooperate with each other to allow installing and removing cover or needle cap 234 without contaminating portions of an associated penetrator.

The dimensions and configuration of second end 202 of hubs 200, 200a or 200b may be varied to accommodate various insertion sites and/or patients. Hubs 200, 200a and 200b may be satisfactorily used with a wide variety of flanges or other configurations compatible for contacting a patient's skin. Also, second end 202 and associated flange may be used with a wide variety of hubs. The present disclosure is not limited to hubs 200, 200a or 200b, end 202 or the associated flange.

For some applications intraosseous device 160 may be described as a one (1") inch needle set. Collar 170 may have a diameter of approximately four (4 mm) or five (5 mm) millimeters. When used as a sternal intraosseous device for some adults, the distance between second end 202 of hub 200 and the extreme end of tip 211 may be approximately twenty five (25.0 mm) millimeters. The distance between second end 172 of collar 170 and the extreme end of tip 211 maybe approximately eight (8) millimeters. As a result the distance between second end 202 and of hub 200 and second end 172 of collar 170 may be approximately seventeen (17.0 mm) millimeters.

For some applications second end 172 of collar 170 may have an effective surface area large enough to support up to fifty pounds of force without second end 172 of collar 170 penetrating compact bone surrounding an intraosseous space. See for example FIGS. 4, 5A and 5B.

One of the benefits of the present disclosure includes the ability to vary the depth of penetration of an intraosseous device into associated bone and bone marrow. For example spacing between second end 172 of collar 170 and the extreme of tip 211 may be increased or decreased by varying the overall length of collar 170.

Penetrators may be provided in a wide variety of configurations and sizes depending upon intended clinical purposes for insertion of the associated penetrator. Outer penetrators may be relatively small for pediatric patients, medium size for adults and large for oversize adults. By way of example, an outer penetrator may range in length from five (5) mm to thirty (30) mm. The diameter of an outer penetrator may range from eighteen (18) gauge to ten (10) gauge.

The length and diameter of an outer penetrator used in a particular application may depend on the size of a bone to which the apparatus may be applied. For example the length of outer penetrator 210 and inner penetrator 220 may be selected for compatibility with a typical adult tibia or humerus, approximately one (1") inch. Placing collar 170 on exterior portions of outer penetrator 210 allows the same penetrators 210 and 220 to be satisfactorily used to access bone marrow in an adult sternum by limiting the depth of penetration to approximately eight (8) millimeters.

Figure 3A:
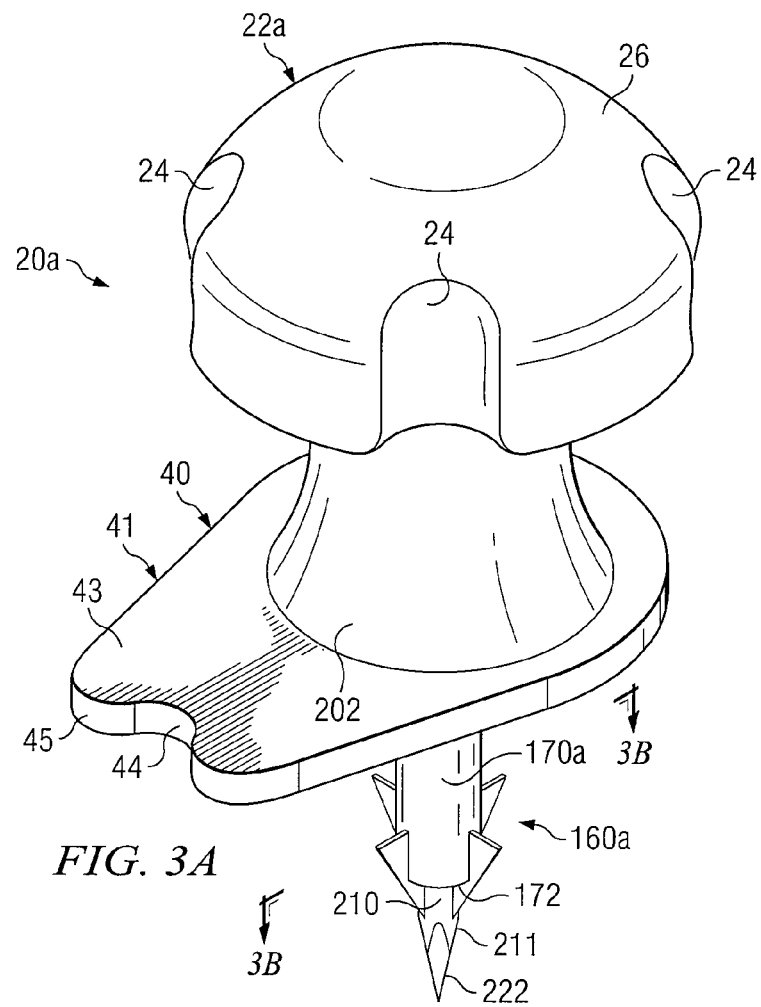
FIG. 3A is a schematic drawing showing an isometric view of an alternate embodiment of apparatus operable to form an incision in soft tissue and to access sternal bone marrow.
Figure 3B:
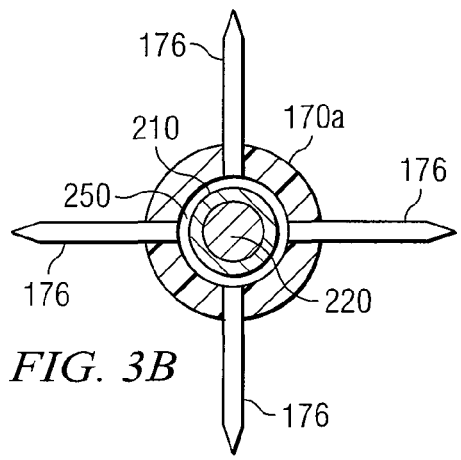
FIG. 3B is a schematic drawing in section taken along lines 3B-3B of FIG. 3A.
Figure 3C:
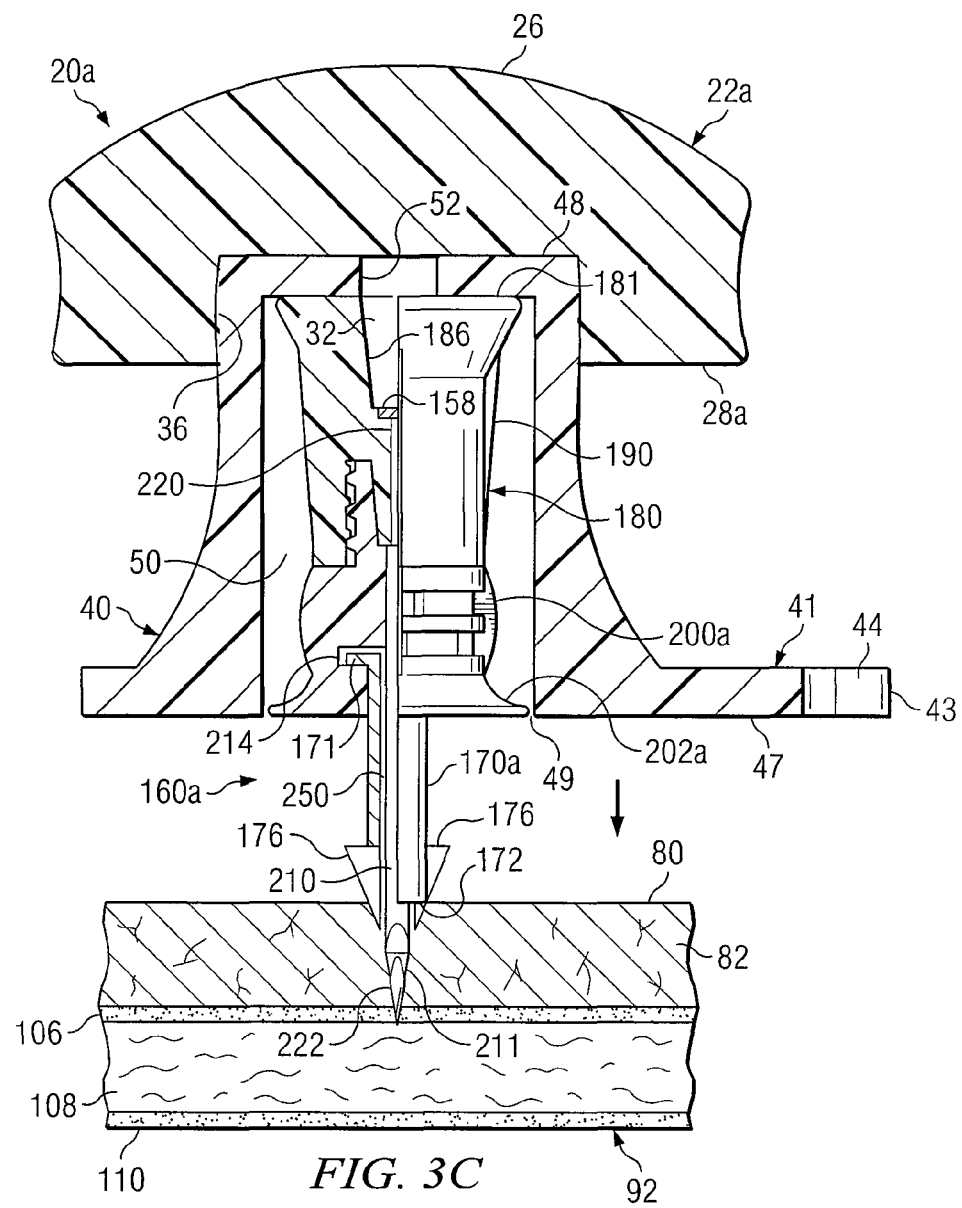
FIG. 3C is a schematic drawing in section with portions broken away of the apparatus of FIG. 3A, wherein the soft tissue penetrator has formed an incision in skin, muscle or other soft tissue prior to inserting an intravenous device through portions of an anterior cortex and entering an adjacent intraosseous space.

For some applications a guide mechanism or template incorporating technique of the present disclosure may be provided to assist with inserting an intraosseous device at a selected insertion site. For embodiments such as shown in FIGS. 3A, 3B and 3C guide mechanism or template 40 may be generally described as having first portion or base 41 with second portion 42 extending therefrom. The configuration and dimensions associated with first portion or base 41 may be selected to be compatible with placing guide mechanism 40 on a patient's chest.

First portion 41 may have a general circular configuration with elongated segment 43 extending therefrom. Notch 44 may be formed adjacent extreme end 45 of elongated segment 43. The dimensions and configuration of notch 44 may be selected to be compatible with sternal notch 104 formed in manubrium 92.

First portion 41 of guide mechanism or template 40 may include surface 47 compatible with contacting a sternum or other insertion site. Opening 49 may be formed in first surface 47 and may extend therethrough. The dimensions and configuration of opening 49 may be selected to be compatible with the exterior dimensions of intraosseous device 160a.

Second portion 42 of guide mechanism or template 40 may be disposed adjacent to opening 49 and extend from base 41 opposite surface 47. Generally elongated cylindrical cavity 50 may be formed in second portion 42 and may be aligned with opening 49 in first portion 41. The dimensions and configuration of cylindrical cavity 50 and opening 49 may be selected to be compatible with placing connector 180 and hub 200 of intraosseous device 160a therein. For embodiments such as shown in FIG. 3C second end 202 of hub 200 may be generally aligned with exterior surface 47 of first portion 41.

Handle 22a may include generally circular recess or cavity 36 extending from second surface 28a. The dimensions and configuration of recess or cavity 36 may be selected to be compatible with placing end 48 of second portion 42 therein. End 48 of second portion 42 may include opening 52.

The dimensions and configuration of opening 52 may be selected to allow inserting portions of drive shaft 32 therethrough. The dimensions and configuration of recess portion or cavity 36 in handle 22a and exterior dimensions of second portion 42 adjacent to end 48 may be selected to allow handle 22a to rotate drive shaft 32 and attach intraosseous device 160a while guide mechanism 40 is held in a generally fixed position with notch 44 aligned with sternal notch 104.

For some applications the finger of an operator (not expressly shown) may be placed in contact with both notch 44 and sternal notch 104 while rotating handle 22a to insert portions of penetrator assembly 160a at a desired insertion. The spacing between notch 44 and the center of cavity 50 may be selected to be approximately equal the space between sternal notch 104 and the center of insertion site 100 or insertion site 102. For embodiments such as shown in FIG. 3C the spacing between notch 44 and the center of cavity 50 may be approximately two centimeters. This spacing may be selected to be compatible with insertion site 100 in manubrium 92.

For some applications notch 44 may be used to position guide mechanism 40 and intraosseous device 160a within insertion site 100 in manubrium 92. For other applications the length of segment 43 may be increased such that notch 44 may be satisfactorily used to position guide mechanism 40 and intraosseous device 160a within insertion site 102 of gladiolus 94.

For embodiments such as shown in FIG. 3C manubrium 92 may include anterior cortex 106, posterior cortex 110 with bone marrow 108 disposed there between. As shown in FIGS. 3A, 3B and 3C, intraosseous device 160a may have similar features and characteristics as previously described for intraosseous device 160 except for modifications to hub 200a and collar 170a. For example, collar 170a may be formed from the same or similar materials as used to form collar 170 or may be formed from materials the same or similar to hub 200a. Collar 170a may have an inside diameter larger than the outside diameter of outer penetrator 210. The difference in diameter may result in forming annular space 250 between the exterior of outer penetrator 210 and interior of collar 170a. See FIGS. 3B and 3C.

For some applications first end 171a of collar 170a may be rotatably engaged with adjacent portions of hub 200a. For embodiments such as shown in FIGS. 3A, 3B and 3C annular recess or annular groove 214 may be formed in hub 200a spaced from second end 202a. First end 171a may include annular projection or annular flange 174 extending radially therefrom. The configuration and dimensions of flange 174 may be selected to be smaller than corresponding configuration and dimensions of annular recess 214. As a result, intraosseous device 160a and particularly hub 200a may rotate relative to collar 170a and first end 171a.

For some applications one or more blades 176 may be disposed in respective slots formed adjacent to second end 172 of collar 170. Blades 176 may be used to form a small incision in skin 80 and muscle or other soft tissue 82 covering insertion site 100 on manubrium 92 or any other insertion site. The dimensions and configuration of blades 176 may be selected to provide a properly sized incision to accommodate inserting removable collar 170a therethrough. Blades 176 remain generally stationary relative to collar 170a. Blades 176 may also be spaced from the exterior of outer penetrator 210 to accommodate rotation of outer penetrator 210 during insertion into bone marrow 108.

Manual driver 20a may be used to insert intraosseous device 160a into bone marrow 108 until second end 172 contacts adjacent portions of anterior cortex layer 106. As a result of annular space 250 formed between exterior portions of outer penetrator 210 and collar 170a including attached blades 176 and by rotatably attaching first end 171a of collar 170a with annular recess 214 of hub 200, collar 170a and associated blades 176 may remain in a relatively fixed location while inserting intraosseous device 160a into associated bone marrow. Annular space 250 and the rotatable connection at first end 171a help to limit any additional cutting or tearing of skin 80 and soft tissue 82 during rotation of intraosseous device 160a.

For some applications a spring or other mechanism (not expressly shown) may be disposed within handle 22a to assist with rotation of intraosseous device 160a. Various types of trigger mechanisms (not expressly shown) may also be provided to allow rotation of drive shaft 32 when guide mechanism 40 has been disposed over a desired insertion site.

Figure 4:
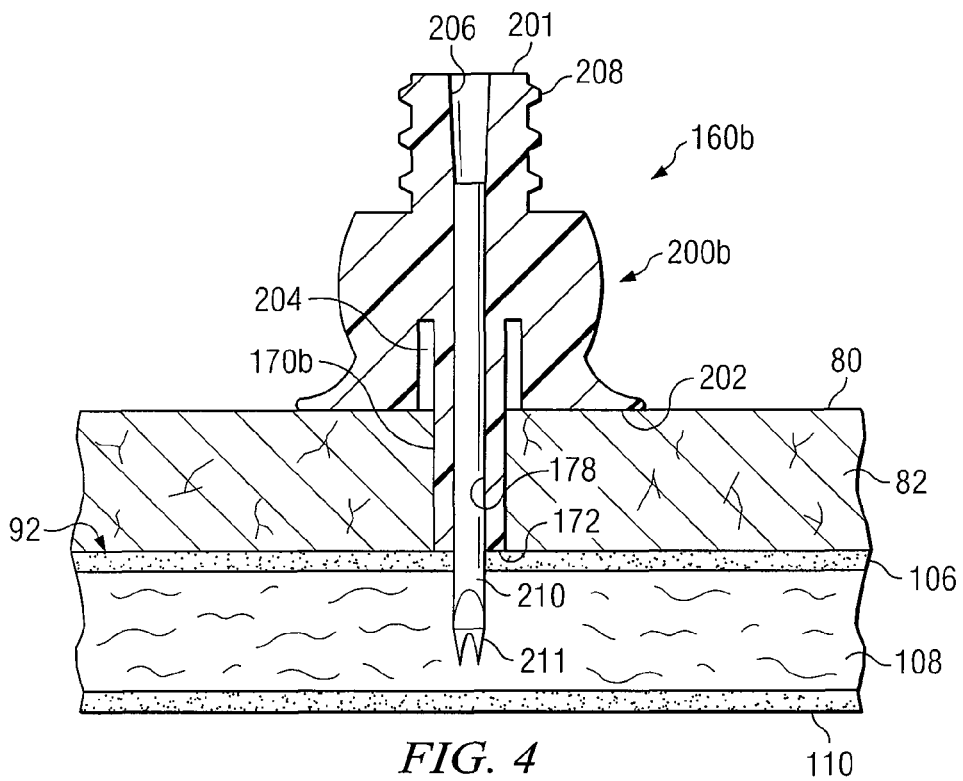
FIG. 4 is a schematic drawing in section with portions broken away showing an intravenous device inserted to a controlled depth into sternal bone marrow in accordance with teachings of the present disclosure.
Figure 5A:
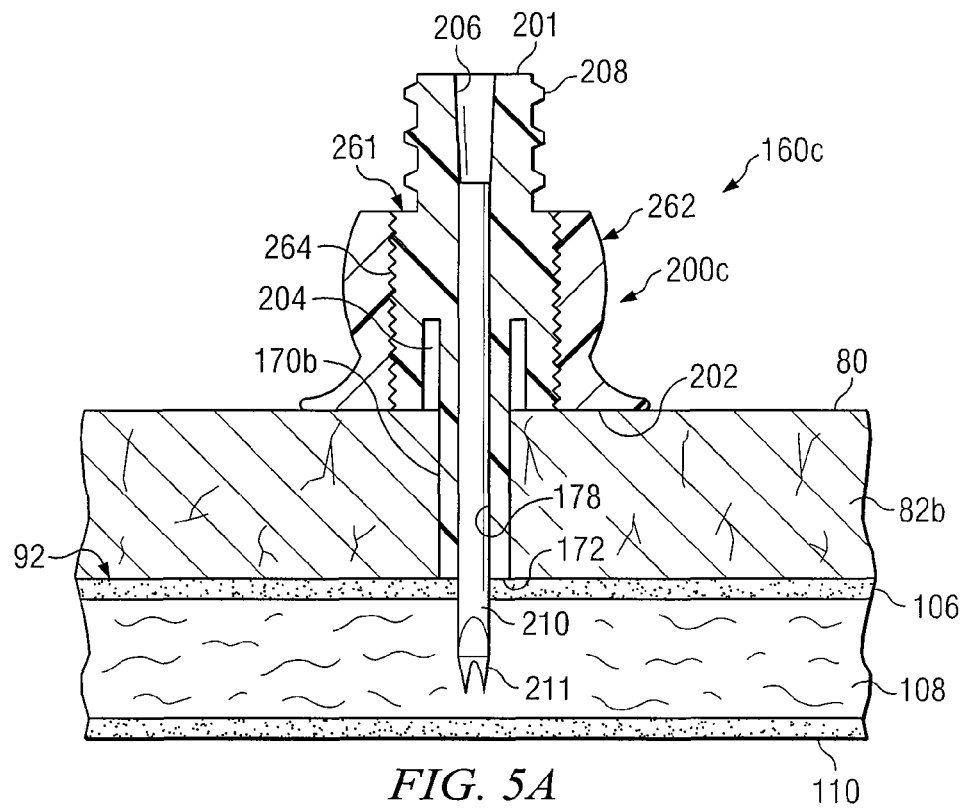
FIG. 5A is a schematic drawing in section with portions broken away showing another example of an intraosseous device inserted at a first intersection site to a controlled depth in sternal bone marrow in accordance with teachings of the present disclosure.
Figure 5B:
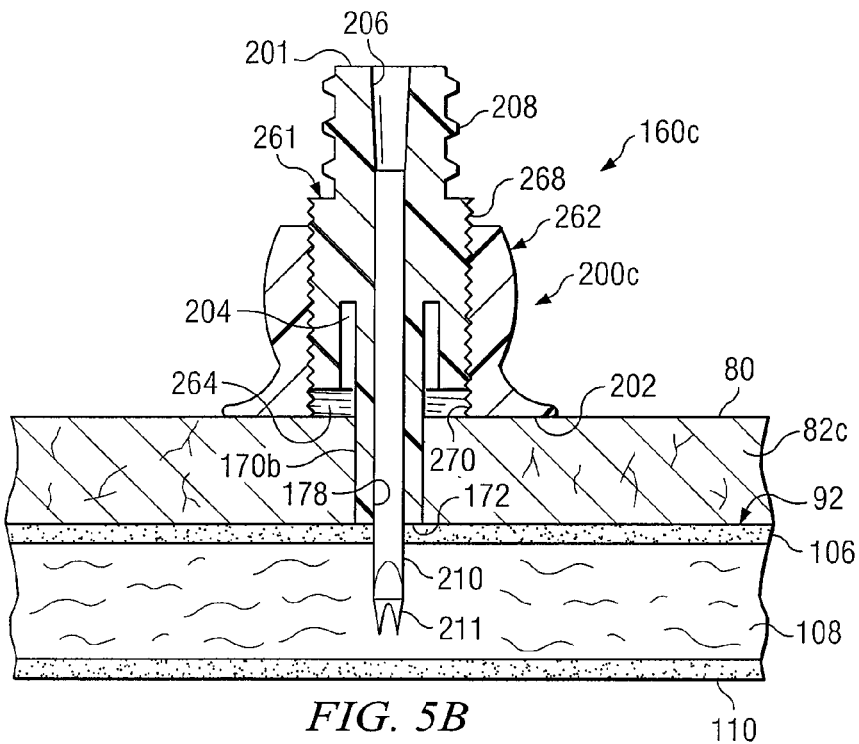
FIG. 5B is a schematic drawing in section with portions broken away showing the intraosseous device of FIG. 5A inserted at a second insertion site to approximately the same controlled depth in sternal bone marrow as shown in FIG. 5A in accordance with teachings of the present disclosure.
Figure 5C:
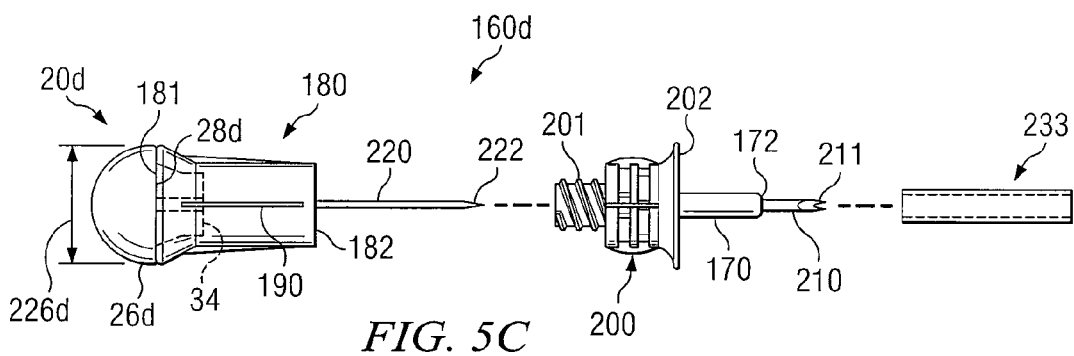
FIG. 5C is a schematic drawing showing an exploded view of apparatus operable to access bone marrow of a sternum in accordance with teachings of the present disclosure.
Figure 5D:
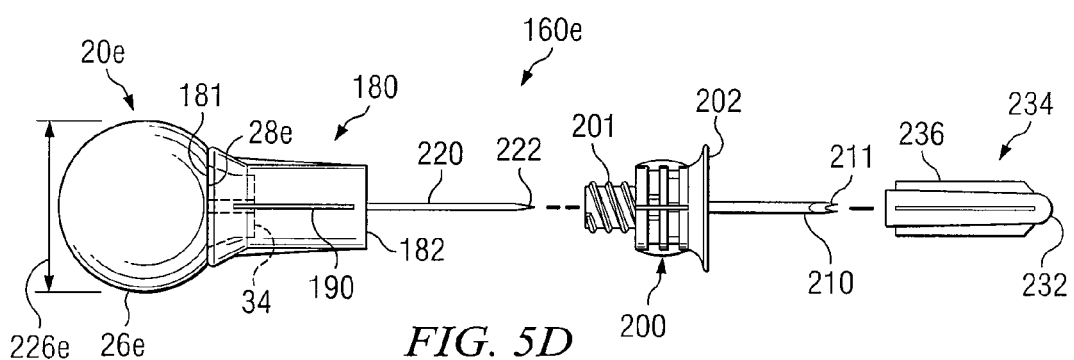
FIG. 5D is a schematic drawing showing an exploded view of another example of apparatus operable to access bone marrow in accordance with teachings of the present disclosure.

For embodiments such as shown in FIGS. 4, 5A and 5B collar 170b may be formed as an integral component of associated hub 200b or 200c. For such embodiments collar 170b may be formed from the same or similar materials used to form other portions of associated hubs 200b and 200c. For some applications collar 170b may be formed as a separate component and a first end of collar 170b (not expressly shown) may be securely engaged with adjacent portions of hubs 200b or 200c. Collar 170b may include inside diameter 178 compatible with contacting exterior or outside diameter portions of outer penetrator 210.

For embodiments such as shown in FIG. 4, the length of collar 170b extending from second end or flange 202 may be selected to provide an optimum spacing between second end 172 and second end 202 of hub 200b corresponding with an "average" thickness of skin, muscle and other soft tissue covering an adult sternum. The spacing between second end 172 of collar 170b and the extreme end of tip 211 of outer penetrator 210 remains fixed or constant for hub 200b. As discussed later, this same spacing may be variable to allow hub 200c to accommodate injection sites having variations in thickness of skin 80 and soft tissue 82 covering each injection site. Second end 172 of collar 170b may provide portions of a depth control mechanism for outer penetrator 210 extending from hub 200b.

For embodiments such as shown in FIGS. 5A and 5B hub 200c may be formed from first segment 261 and second segment 262. First segment 261 may include first end 201 with first longitudinal bore 206 extending therethrough. Outer penetrator 210 may be securely engaged with first segment 261. Second segment 262 may include second end 202 of hub 200c. Second segment 262 may be generally described as having longitudinal bore 264 extending therethrough.

As shown in FIGS. 5A and 5B first segment 261 may have exterior dimensions sized to fit within second longitudinal bore 264 of second segment 262. First threads 268 may be formed on exterior portions of first segment 261. Second threads 270 may be formed on interior portions of second longitudinal bore 264 of second segment 262. First threads 268 and second threads 270 may have matching thread profiles. As a result threads 268 of first portion 261 of hub 200b may be engaged with threads 270 of second portion 262.

Rotation of first segment 261 relative to second segment 262 may be used to vary spacing between second end 172 of collar 170b and associated second end or flange 202 of hub 200c. Compare FIGS. 5A and 5B with each other. As a result, hub 200c may be used at various injection sites and target areas and/or may be used with patients having increasing or decreasing thickness of soft tissue covering an insertion site as compared with an average thickness for an adult sternum.

For some applications the length of collar 170b extending from second end 202 of hub 200c may be increased as compared with the length of collar 170b extending from hub 200b. The increased length of collar 170b may be used to accommodate soft tissue 82b which is thicker than soft tissue 82 as shown in FIG. 4. Intraosseous device 160c and particularly hub 200c may also be satisfactorily used at injection sites which have a reduced thickness of skin and soft tissue covering an injection site. See for example FIG. 5B. For this embodiment the thickness of muscle and other soft tissue 82c may be less than the "average" thickness shown in FIG. 4. When intraosseous device 160c is initially installed at an insertion site such as shown in FIG. 5A, a gap or space would be apparent between second 202 and skin 80. The threaded connection formed between first segment 261 and second segment 262 allows rotation of second segment 262 until second surface or flange 202 contacts skin 80 at the injection site. See FIG. 5B. As a result, hub 200c may provide desired stabilization for outer penetrator 210 and other portions of intraosseous device 160c at insertion sites with variations from "average" thickness of skin and other soft tissue covering the insertion site.

FIG. 5C shows one example of an intraosseous device incorporating teachings of the present disclosure operable to provide intraosseous access to bone marrow disposed in a sternum. Intraosseous device 160d as shown in FIG. 5C may include connector 180, hub 200, collar 170, outer penetrator 210 and inner penetrator 220 as previously described with respect to FIGS. 2A, 2B and 2C.

For some applications manual driver 20d may be securely engaged with intraosseous device 160d. Manual driver 20d may also have substantially reduced dimensions as compared with manual drivers 20 and 20a. Reducing the dimensions and configuration associated with manual driver 20d may limit the amount of force which may be applied to intraosseous device 160d by personnel trying to obtain IO access to safe levels, particularly during an emergency or other stressful conditions.

For embodiments such as shown in FIG. 5C manual driver 20d may include handle 22d defined in part by generally dome shaped portion or spherical portion 26d extending from surface 28d. For some applications exterior dimensions and configuration of surface 28d may be approximately equal to the dimensions and configuration of first end 181 of associated connector 180. For example, the diameter of surface 28d may correspond approximately with the diameter of spherical portion 26d and may also approximately equal the diameter of first end 181 of connector 180. See arrow 226d in FIG. 5C. Spherical portion 26d may also be formed as an integral component of connector 180 (not expressly shown) opposite from end 182. Such embodiments would not include respective surfaces 28d and 181.

FIG. 5D shows another example of an intraosseous device incorporating teachings of the present disclosure operable to provide intraosseous access to bone marrow adjacent to a selected insertion site. Intraosseous device 160e as shown in FIG. 5D may include connector 180, hub 200, outer penetrator 210 and inner penetrator 220 as previously described with respect to FIGS. 2A, 2B, 2C and 5C. However, intraosseous device 160e does not include collar 170. As a result, intraosseous device 160e may be used at locations other than a sternum. Such locations may include, but are not limited to, a humerus or upper tibia.

For some applications manual driver 20e may be securely engaged with intraosseous device 160e. Manual driver 20e may also have substantially reduced dimensions as compared with manual drivers 20 and 20a. However, the dimensions of manual driver 20e may be larger than corresponding dimensions of driver 20d. As a result, manual driver 20e may accommodate inserting intraosseous device 160e at locations such as a humerus or upper tibia. Manual driver 20e may allow applying more force to intraosseous device 160e than manual driver 20d may be operable to apply to intraosseous device 160d.

For embodiments such as shown in FIG. 5D manual driver 20e may include handle 22e defined in part by generally dome shaped portion or spherical portion 26e extending from surface 28e. For some applications exterior dimensions and configuration of surface 28e may be approximately equal to the dimensions and configuration of first end 181 of associated connector 180. For example, the diameter of surface 28e may be approximately equal to the diameter of first end 181 of connector 180. However, the diameter of spherical portion 26e may be larger than the diameter of surface 28e or first end 181. See arrow 226e in FIG. 5D. Spherical portion 26e may also be formed as an integral component of connector 180 opposite from end 182. Such embodiments would not include respective surfaces 28e and 181.

Another aspect of the present disclosure may include providing various types of packaging and/or kits for intraosseous devices in accord to the teachings of the present disclosure. Such kits may also be referred to as "containers" or "canisters". See for example FIGS. 6A, 6B and 6C. Various molding techniques may be used to form such kits.

Figure 6A:
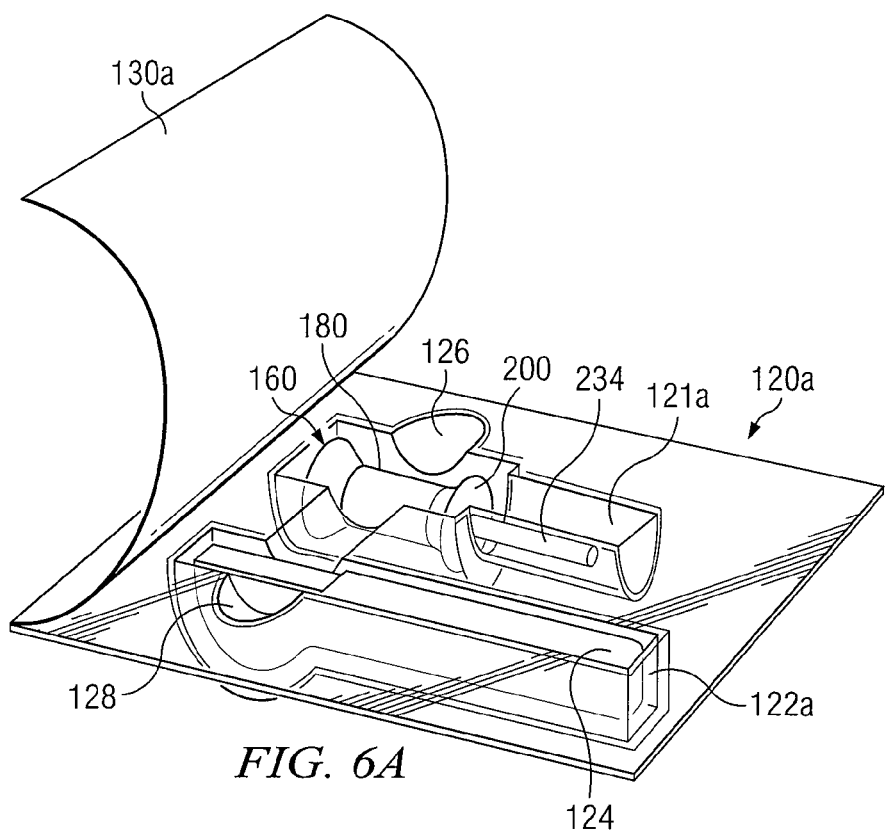
FIG. 6A is a schematic drawing showing one example of packaging for an IO needle set operable to penetrate a bone and associated bone marrow along with a scalpel operable to form an incision in soft tissue covering an insertion site.

For embodiments such as shown in FIG. 6A kit or packaging 120a may include first recess 121a and second recess 122a. The general configuration and dimensions of first recess 121a may be selected to accommodate placing intraosseous device 160 therein. The general configuration and dimensions of second recess 122a may be selected to be compatible with placing surgical scalpel 124 therein. Indentions or finger cutouts 126 and 128 may also be formed in kit 120a proximate recess 121a and recess 122a to accommodate removing intraosseous device 160 and/or scalpel 124 therefrom. Removable cover 130a may be placed over kit 120a to retain intraosseous device 160 and scalpel 124 in associated recesses 121a and 122a. Kit 120a and/or removable cover 130a may be formed from various types of disposal materials including a wide range of thermoplastic and polymeric materials.

Figure 6B:
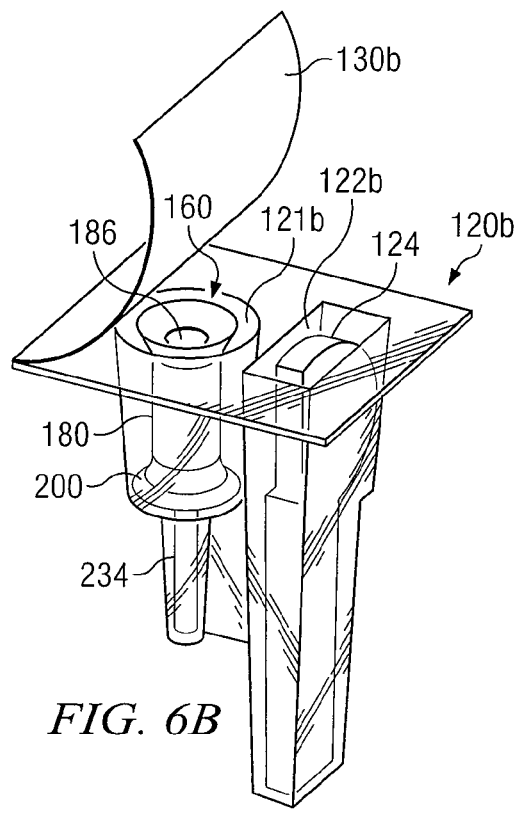
FIG. 6B is a schematic drawing showing another example of packaging for an IO needle set operable to penetrate a bone and associated bone marrow along with a scalpel operable to form an incision in soft tissue covering an insertion site.

For embodiments such as shown in FIG. 6B kit or packaging 120b may include first recess 121b and second recess 122b. First recess 121b may also be referred to as first container 121b. Second recess 122b may also be referred to as second container 122b. The general configuration and dimensions of recess 121b may be selected to accommodate placing intraosseous device 160 therein. The general configuration and dimensions of second recess 122b may be selected to be compatible with placing scalpel 124 therein. Removable cover 130b may be placed over kit 120b to retain intraosseous device 160 and scalpel 124 in associated recesses or containers 121b and 122b. Kit 120b and/or removable cover 130b may be formed from various types of disposal materials including a wide range of thermoplastic and polymeric materials.

Figure 6C:
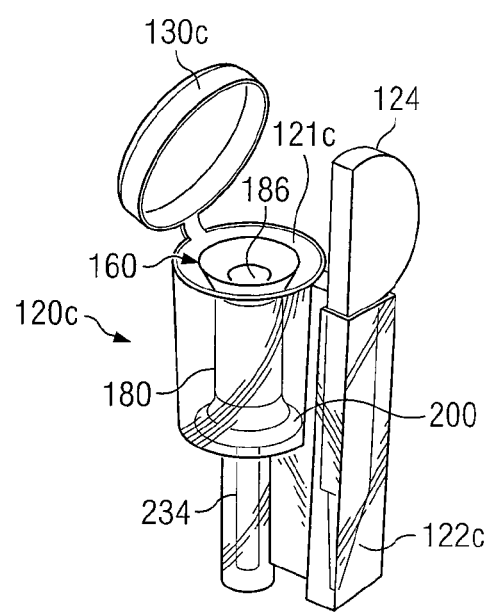
FIG. 6C is a schematic drawing showing still another example of packaging for an IO needle set operable to penetrate a bone and associated bone marrow along with a scalpel operable to form an incision in soft tissue covering an insertion site.

For embodiments such as shown in FIG. 6C kit or packaging 120c may include first recess 121c and second recess 122c. First recess 121c may also be referred to as container 121c. Second recess 122c may also be referred to as container 122c. The general configuration and dimensions of recess 121c may be selected to accommodate placing intraosseous device 160 therein. The general configuration and dimensions of second recess 122b may be selected to be compatible with placing at least portions of scalpel 124 therein. Removable cover or lid 130c may be placed over recess 121c to retain intraosseous device 160 therein. Kit 120c and/or removable cover or lid 130c may be formed from various types of disposal materials including a wide range of thermoplastic and polymeric materials.

For some applications containers 121c and 122c may be formed as separate components (not expressly shown). Alternatively, dual cylinders (not expressly shown) similar to container 121c with respective lids 130c may be used to hold an IO device in one container and a scalpel in the other container. Adhesive tape, shrink wrap or other suitable wrapping materials (not expressly shown) may be used to attach such separate containers with each other. Labels (not expressly shown) may also be placed on such kits to indicate IO devices appropriate for sternal access, adult access in a tibia or humerus, or pediatric procedures.

Figure 7:
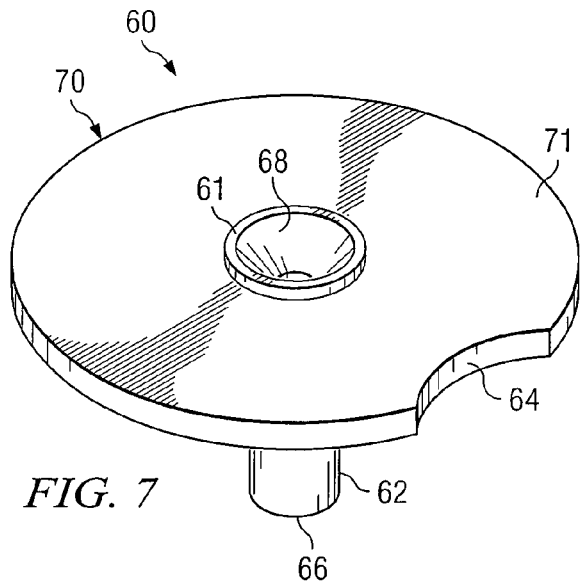
FIG. 7 is a schematic drawing showing an isometric view of apparatus operable to guide penetration of an IO needle set into bone marrow and to limit the depth of such penetration into the bone marrow in accordance with teachings of the present disclosure.

Another aspect of the present disclosure may include providing a combined guide and/or depth control mechanism operable to install an intraosseous device at a selected insertion site in accordance with teachings of the present disclosure. For example, a combined guide and depth control mechanism such as shown in FIGS. 7, 8B and 8C may be satisfactorily used to insert an intraosseous device into bone marrow adjacent to a selected insertion site. Combined guide and depth control mechanism 60 may include generally elongated, hollow portion 62 which may be inserted into an incision formed in soft tissue covering an insertion site. See FIGS. 8A and 8B.

Elongated, hollow portion 62 may sometimes be referred to as a collar or depth limiter. For some applications elongated, hollow portion 62 may include first end 61 with enlarged portion 70 extending therefrom. Enlarged portion 70 may be operable to limit movement of an intraosseous device through elongated, hollow portion 62. Second end 66 of elongated, hollow portion 62 may be sized to engage an anterior cortex at a selected insertion site.

For some embodiments enlarged portion 70 of combined guide and depth control mechanism 60 may be generally described as a circular disk having first surface 71 and second surface 72. Enlarged portions with other configurations may be formed proximate first end 61 of elongated, hollow portion 62. Elongated, hollow portion 62 may extend from second surface 72 opposite from first surface 71. Elongated, hollow portion 62 may include longitudinal bore or longitudinal passageway 74 extending therethrough.

Opening 68 may be formed in enlarged portion 70 adjacent to and aligned with longitudinal passageway 74. Opening 68 and longitudinal passageway 74 may be sized to received portions of an associated intraosseous device. See FIG. 8C. For some embodiments opening 68 may have a generally tapered or funnel shaped configuration to assist in guiding one end of a intraosseous device therethrough.

Figure 8A:
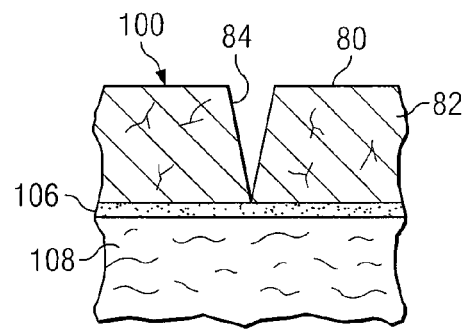
FIG. 8A is a schematic drawing in section with portions broken away of an incision made in soft tissue covering a selected insertion site for inserting an IO needle set into a target area in accordance with teachings of the present disclosure.
Figure 8B:
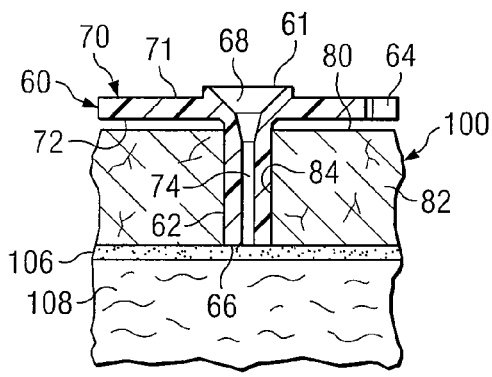
FIG. 8B is a schematic drawing in section with portions broken away showing one example of a combined guide and/or depth control mechanism incorporating teachings of the present disclosure disposed in soft tissue at the insertion site shown in FIG. 8A.
Figure 8C:
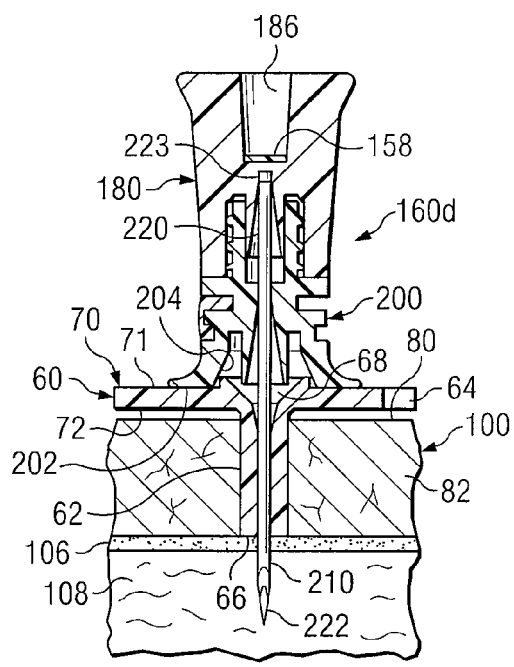
FIG. 8C is a schematic drawing in section with portions broken away showing portions of an IO needle set disposed in bone marrow at the target area in accordance with teachings of the present disclosure.

For some embodiments such as shown in FIGS. 8A, 8B and 8C, a scalpel may be used to form incision 84 in skin 80 and muscle or other soft tissue 82 adjacent to insertion site 100 covering manubrium 92. Elongated, hollow portion 62 of combined guide and depth control mechanism 60 may then be inserted into incision 84 until second end 66 contacts anterior cortex 106 at insertion site 100. Incision 84 may be similar to an incision used to access a sternum.

Enlarged portion 70 of combined guide and depth control mechanism 60 may include notch 64 disposed in an exterior portion thereof. The configuration and dimensions of notch 64 may be generally compatible with notch 104 in manubrium 92. Prior to forming incision 84 at insertion site 100, portions of an operator's finger (not expressly shown) may be placed in both notch 64 and notch 104 to align combined guide and depth control mechanism 60 with a desired insertion site. A scalpel may then be used to form an incision at the indicated location for inserting collar 62.

After installing portions of combined guide and depth control mechanism 60 within incision 84, various intraosseous devices may be inserted through longitudinal passageway 74. For some embodiments such as shown in FIG. 8C, portions of intraosseous device 160d may be inserted through longitudinal passageway 74. Intraosseous device 160d and a scalpel satisfactory for forming incision 84 may be obtained from a kit or packaging such as in FIG. 6A, 6B or 6C. Intraosseous device 160d may be similar to previously described intraosseous device 160. However, intraosseous device 160d does not include collar or depth control limiter 170. Collar 62 may sometimes be referred to as a "removable depth limiter".

Portions of outer penetrator 210 and associated inner penetrator 220 may be inserted through opening 68 and longitudinal passageway 74. Manual drivers 20, 20d or an other suitable driver may be engaged with connector receptacle 186 to insert portions of intraosseous device 160d into adjacent bone marrow 108. Insertion of intraosseous device 160d may continue until second end or flange 202 of hub 200 contacts first surface 71 of combined guide and depth control mechanism 60. For some applications the extreme end of penetrators 210 and/or 220 may extend approximately eight (8 mm) millimeters from end 66 of elongated, hollow portion 62 when second end 202 of IO device 160d is resting on first surface 71 of enlarged portion 70.

Although the present disclosure and its advantages have been described in detail, it should be understood that various changes, substitutions and alternations can be made herein without departing from the spirit and scope of the disclosure as defined by the following claims.

What is claimed is:

1. Apparatus for accessing bone marrow of a sternum comprising: a intraosseous device having a penetrator with a tip operable to penetrate the sternum; a driver operable to insert a portion of the intraosseous device into the sternum, the driver having an exterior surface configured to be grasped by the user; wherein the driver further comprises: a handle having a first surface with a generally dome shaped configuration extending from the first surface; the dome shaped portion ergonomically designed to fit the palm of an operator; and a connector extending from the first surface of the handle; and the connector operable to releasably engage the driver with the intraosseous device; a guide operable to locate the driver and intraosseous device at an insertion site on the sternum; the guide having an elongated cavity operable to receive a portion of the intraosseous device therein; the elongated cavity in the guide defined in part by a first opening operable to receive the portion of the intraosseous device therethrough; and the elongated cavity in the guide having a second opening sized to accommodate releasably engaging the driver with the intraosseous device and to accommodate inserting the intraosseous device into the sternum using the driver; where the apparatus is configured such that the distance between the tip and the exterior surface of the driver will remain substantially constant during insertion of the intraosseous device into the sternum.

2. The apparatus of claim 1 further comprising a depth limiter operable to control depth of penetration of the intraosseous device into the sternum.

3. The apparatus of claim 1 wherein the driver further comprises a handle having a generally circular configuration.

4. The apparatus of claim 1 wherein the guide further comprises:
a first surface operable to be disposed on the sternum; and
a notch formed in one end of the first surface.

5. The apparatus of claim 1 wherein the depth control mechanism further comprises a collar disposed on an exterior portion of the intraosseous device.

6. The apparatus of claim 1 further comprising a depth control mechanism operable to limit depth of penetration of the intraosseous device into the sternum.

7. The apparatus of claim 6 wherein the depth control mechanism further comprises:
a collar having a generally elongated, hollow configuration;
the collar disposed on an exterior portion of the intraosseous device;
a plurality of longitudinal slots formed in the exterior of the collar;
a respective blade disposed in each slot; and
the blades operable to form incisions in skin, muscle and other soft tissue covering the desired injection site.

8. The apparatus of claim 7 further comprising portions of the intraosseous device, while being inserted into the sternum, operable to rotate relative to the collar.

9. The apparatus of claim 1, further comprising a plurality of finger grips formed in exterior portions of the handle.

10. Apparatus for accessing bone marrow proximate an insertion site comprising:
a driver operable to insert an intraosseous device into the bone marrow, the intraosseous device including at least a cannula;
the driver having a handle with an exterior surface configured to be grasped by the user and a connector extending from the handle, where the connector is configured to releasable secure the handle relative to the cannula;
the intraosseous device disposed in a kit prior to engagement with the driver;
the intraosseous device having a tip;
the driver and intraosseous device being configured such that distance between the tip and the exterior surface of the driver will remain substantially constant during insertion of the intraosseous device;
a scalpel disposed in the kit; and
the scalpel operable to form an incision in soft tissue covering the insertion site after removing the scalpel from the kit.

11. The apparatus of claim 10 further comprising:
the driver having a handle with a connector extending therefrom; and
the intraosseous device having a connector receptacle operable to be releasably engaged with the connector of the driver.

12. The apparatus of claim 10 further comprising:
a removable cover placed over the first recess and the second recess to retain the intraosseous device and the scalpel therein until the cover has been removed from the kit; and
the kit and the cover formed from disposable material.

13. The apparatus of claim 10 wherein the first recess further comprises:
a first container operable to receive the intraosseous device; and
a removable cover placed over the container to retain the intraosseous device in the first container.

14. The apparatus of claim 13 wherein the second recess further comprises:
a second container operable to receive at least a portion of the scalpel therein; and
the first container and the second container engaged with each other.

15. Apparatus for accessing bone marrow of a sternum comprising: an intraosseous needle set configured to penetrate the sternum and provide access to the bone marrow of the sternum; a driver operable to insert the IO needle set into the bone marrow of the sternum; a guide mechanism operable to stabilize the intraosseous needle set during insertion into the bone marrow of the sternum; the guide mechanism including a generally hollow, cylindrical portion operable to be inserted into an incision formed in soft tissue covering the sternum; the generally hollow, cylindrical portion having an inside diameter operable to receive portions of the intraosseous needle set therein and to allow rotation of the intraosseous needle set during insertion relative to the generally hollow, cylindrical portion; a generally disk shaped portion with the hollow, cylindrical portion extending therefrom and unitary with the generally disk shaped portion; an opening formed in the disk shaped portion adjacent to and communicating with the elongated cylindrical portion; and the opening formed in the disk having a generally coned shaped surface operable to guide one end of the intraosseous needle set therethrough.

16. The apparatus of claim 15 wherein the intraosseous needle set further comprises an outer cannula and an inner stylet.

17. The apparatus of claim 16 wherein the hollow, cylindrical portion comprises an elongated collar surrounding the cannula.

18. An intraosseous device operable to penetrate a bone and associated bone marrow comprising:
a hub having a first end operable to be releasably engaged with a connector and a second end operable to be disposed adjacent to an insertion site for the intraosseous device;
a first opening formed in the first end of the hub;
a first longitudinal bore extending from the first opening through the hub to a second opening formed in the second end of the hub;
an outer penetrator having a first end securely disposed within the longitudinal bore of the hub proximate the first opening in the hub;
the outer penetrator having a second end extending from the second opening of the hub;
a depth limiter having a first end engaged with the hub;
the depth limiter disposed around exterior portions of the outer penetrator extending from the second end of the hub; and
a second end of the depth limiter spaced a selected distance from a tip of the intraosseous device.

19. The apparatus of claim 18 further comprising:
a Luer lock connection formed on the first end of the hub; and
the Luer lock connection operable to accommodate attaching the first end of the hub to a fluid source.

20. The intraosseous device of claim 18 further comprising:

the first end of the hub formed on a first segment of the hub;
the first longitudinal bore extending through the first segment of the hub;
the second end of the hub formed on a second segment of the hub;
the second segment of the hub having a second longitudinal bore extending therethrough;
the first segment of the hub having exterior dimensions sized to fit within the second longitudinal bore of the second segment of the hub;
a first set of threads formed on exterior portions of the first segment of the hub;
a second set of threads form on interior portions of the second longitudinal bore;
the first portion of the hub threadably engaged with the second portion of the hub;
a first end of the outer penetrator disposed proximate the first end of the first portion of the hub; and
the first set of threads and to cooperate with the second set of threads operable to cooperate with each other to vary the distance between the second end of the depth limiter and the second surface of the hub.

21. The apparatus of claim 18 further comprising a removable inner penetrator disposed within the first longitudinal bore of the first portion of the hub.

22. Apparatus for accessing bone marrow in a sternum comprising: a driver operable to insert an IO needle set into the bone marrow of the sternum; the intraosseous needle set operable to penetrate the sternum and provide access to bone marrow of the sternum; the intraosseous needle set including an outer cannula having a tip and an inner trocar; a hub having a flange operable to stabilize the intraosseous needle set after inserting the intraosseous needle set into the bone marrow in the sternum where the hub is configured to be removably coupled to the driver; and a collar extending from the hub to a distal end disposed between the flange and the tip, the collar disposed around and in non-adjustably fixed relation to the cannula such that the distal end of the collar is configured to limit depth of penetration of the intraosseous needle set into the bone marrow of the sternum; where the apparatus is configured such that the distance between the distal end of the collar and the tip of the outer cannula will remain substantially constant during insertion of the intraosseous needle set into the sternum.

23. The apparatus of claim 22, further comprising: the driver having a handle defined in part by a generally dome shaped portion;
the dome shaped portion extending from a surface having a generally circular configuration defined in part by a first diameter; the intraosseous needle set having a connector defined in part by a first end having a generally circular configuration defined in part by a second diameter; and the first diameter associated with the handle approximately equal to the second diameter associated with the first end of the connector.

24. Apparatus operable to direct and limit depth of penetration of an intraosseous device into bone marrow proximate an insertion site for the intraosseous device, comprising:
an elongated, hollow portion operable to be inserted into an incision formed in soft tissue covering the insertion site;
the elongated, hollow portion having a first end with an enlarged portion of the apparatus disposed adjacent thereto;
the elongated, hollow portion having a second end operable to engage portions of an anterior cortex proximate the insertion site without penetrating the anterior cortex; and
the enlarged portion of the apparatus operable to removably receive a needle set of the intraosseous device to limit movement of the intraosseous device through the elongated, hollow portion.

25. The apparatus of claim 24 wherein the enlarged portion further comprises:
a generally circular disk having a first surface and a second surface;
the elongated, hollow portion extending from the second surface of the disk opposite from the first surface;
the elongated, hollow portion having a longitudinal passageway extending therethrough;
an opening disposed in the disk;
the hole in the disk generally aligned with the longitudinal passageway of the elongated, hollow portion;
the opening and the longitudinal passageway sized to receive portions of the intraosseous device therein.

26. The apparatus of claim 25 further comprising the second surface of the disk operable to support portions of the intraosseous device thereon.

27. Apparatus operable to access bone marrow proximate an insertion site comprising:
an intraosseous device including an outer penetrator, an inner penetrator, and a connector securely engaged with a manual driver;
the manual driver operable to insert portions of the intraosseous device through an anterior cortex of a bone and into adjacent bone marrow;
the manual driver defined in part by a handle; and
the connector configured to releasably secure the handle and inner penetrator relative to the outer penetrator.

28. The apparatus of claim 27 further comprising:
the handle having a generally spherical portion extending from a generally planar surface; and
the generally planar surface of the handle securely engaged with the one end of the connector.

29. The apparatus of claim 28 further comprising the generally planar surface of the handle having a diameter approximately equal to a diameter of the one end of the connector.

30. The apparatus of claim 27 further comprising the manual driver formed as an integral component of the connector.

* * * * *